(12) United States Patent
Ueno et al.

(10) Patent No.: US 9,566,423 B2
(45) Date of Patent: Feb. 14, 2017

(54) TRANSDERMAL PATCH MANUFACTURING METHOD AND TRANSDEMAL PATCH

(71) Applicant: NISSHA PRINTING CO., LTD., Kyoto-shi, Kyoto (JP)

(72) Inventors: Takako Ueno, Kyoto (JP); Chika Kaede, Kyoto (JP); Shinya Yamada, Kyoto (JP); Yoichi Yamaguchi, Kyoto (JP)

(73) Assignee: NISSHA PRINTING CO., LTD., Kyoto (JP)

( * ) Notice: Subject to any disclaimer, the term of this patent is extended or adjusted under 35 U.S.C. 154(b) by 0 days.

(21) Appl. No.: 14/889,130

(22) PCT Filed: Apr. 22, 2014

(86) PCT No.: PCT/JP2014/061227
§ 371 (c)(1),
(2) Date: Nov. 4, 2015

(87) PCT Pub. No.: WO2014/181674
PCT Pub. Date: Nov. 13, 2014

(65) Prior Publication Data
US 2016/0082240 A1  Mar. 24, 2016

(30) Foreign Application Priority Data

May 7, 2013  (JP) .................................. 2013-097660

(51) Int. Cl.
*A61M 37/00* (2006.01)
*B32B 38/00* (2006.01)
(Continued)

(52) U.S. Cl.
CPC ........ *A61M 37/0015* (2013.01); *A61K 9/0021* (2013.01); *B29C 65/48* (2013.01);
(Continued)

(58) Field of Classification Search
CPC .... A61M 37/0015; B29D 99/005; B29D 7/01; B29C 66/022; B29C 65/48; B29C 66/0382; B32B 37/12; B32B 2535/00; B32B 5/18; B32B 38/0012; B32B 3/30; B32B 3/266; B32B 2037/243; A61K 9/0021; B29K 2995/0068; B29K 2995/0069
See application file for complete search history.

(56) References Cited

U.S. PATENT DOCUMENTS 4,614,787 A   9/1986  Szycher et al.
4,638,043 A   1/1987  Szycher et al.
(Continued)

FOREIGN PATENT DOCUMENTS

JP   S62-47372 A      3/1987
JP   2004-209074 A    7/2004
(Continued)

OTHER PUBLICATIONS

International Search Report in PCT/JP2014/061227 dated Jul. 29, 2014.

*Primary Examiner* — Emily Schmidt
*Assistant Examiner* — Lauren M Peng
(74) *Attorney, Agent, or Firm* — Global IP Counselors, LLP

(57) ABSTRACT

A low cost transdermal patch comprises water soluble microneedles and has good performance. A transdermal patch comprises a microneedle sheet, which comprises a plurality of water soluble microneedles, moisture permeable sheet, wherethrough water vapor passes, and a reinforcing film. The reinforcing film is adhered, by an adhesive layer having an adhesive strength less than that of an adhesive layer, onto an outer surface of the moisture permeable sheet, which is the side opposite the skin opposing surface. The reinforcing film includes a water vapor barrier sheet, which (Continued)

blocks the passage of water vapor through at least a first area, and a removable portion around the water vapor barrier sheet. The removable portion is configured such that it can be separated from and peeled off the water vapor barrier sheet.

11 Claims, 10 Drawing Sheets

(51) Int. Cl.
| | |
|---|---|
| *B29C 65/00* | (2006.01) |
| *B29D 7/01* | (2006.01) |
| *B29C 65/48* | (2006.01) |
| *B32B 3/26* | (2006.01) |
| *B29D 99/00* | (2010.01) |
| *B32B 37/12* | (2006.01) |
| *A61K 9/00* | (2006.01) |
| *B29L 7/00* | (2006.01) |
| *B29L 31/00* | (2006.01) |
| *B32B 37/24* | (2006.01) |
| *B32B 3/30* | (2006.01) |
| *B32B 5/18* | (2006.01) |

(52) U.S. Cl.
CPC ........ *B29C 66/022* (2013.01); *B29C 66/0382* (2013.01); *B29D 7/01* (2013.01); *B29D 99/005* (2013.01); *B32B 3/266* (2013.01); *B32B 3/30* (2013.01); *B32B 5/18* (2013.01); *B32B 37/12* (2013.01); *B32B 38/0012* (2013.01); *A61M 2037/0023* (2013.01); *A61M 2037/0046* (2013.01); *A61M 2037/0053* (2013.01); *B29K 2995/0062* (2013.01); *B29K 2995/0068* (2013.01); *B29K 2995/0069* (2013.01); *B29L 2007/001* (2013.01); *B29L 2031/7544* (2013.01); *B32B 2037/243* (2013.01); *B32B 2307/724* (2013.01); *B32B 2307/7246* (2013.01); *B32B 2535/00* (2013.01)

(56) References Cited

U.S. PATENT DOCUMENTS

| | | | |
|---|---|---|---|
| 4,727,868 A | | 3/1988 | Szycher et al. |
| 4,751,133 A | | 6/1988 | Szycher et al. |
| 4,880,690 A | | 11/1989 | Szycher et al. |
| 6,656,147 B1 | * | 12/2003 | Gertsek ............ A61M 5/14248 604/185 |
| 2008/0262444 A1 | | 10/2008 | Takada |
| 2009/0010997 A1 | | 1/2009 | Haley |
| 2009/0182306 A1 | * | 7/2009 | Lee ...................... A61K 9/0021 604/506 |
| 2010/0256568 A1 | * | 10/2010 | Frederickson .... A61M 37/0015 604/173 |
| 2011/0046575 A1 | | 2/2011 | Takada |
| 2013/0018279 A1 | * | 1/2013 | Plante ............... A61B 5/150022 600/583 |
| 2014/0243788 A1 | * | 8/2014 | Cantor ............. A61M 37/0015 604/506 |

FOREIGN PATENT DOCUMENTS

| | | |
|---|---|---|
| JP | 2004-209704 A | 7/2004 |
| JP | 2009-528900 A | 8/2009 |
| JP | 2010-068840 A | 4/2010 |
| JP | 2010-094414 A | 4/2010 |
| JP | 2010-142473 A | 7/2010 |
| JP | 2011-194189 A | 10/2011 |
| JP | 2012-075855 A | 4/2012 |
| WO | 2006/080508 A1 | 8/2006 |

* cited by examiner

TRANSDERMAL PATCH MANUFACTURING METHOD AND TRANSDEMAL PATCH

CROSS-REFERENCE TO RELATED APPLICATION

This U.S. National stage application claims priority under 35 U.S.C. §119(a) to Japanese Patent Application No. 2013-097660, filed in Japan on May 7, 2013, the entire contents of Japanese Patent Application No. 2013-097660 are hereby incorporated herein by reference.

BACKGROUND

Field of the Invention

The present invention relates to a transdermal patch comprising water soluble microneedles and to a method of manufacturing the same.

Background Information

Conventionally, one means of administering a drug or drugs noninvasively via the body surface of an organism, such as the skin or a mucous membrane, is to perform transdermal administration via a transdermal patch. Furthermore, to efficiently adsorb a drug or the like from a transdermal patch onto the body, a preparation called a microneedle sheet or a microneedle patch is being developed whereon the drug is adsorbed by minute needles having a high aspect ratio, which are referred to as so-called microneedles, and those minute needles are disposed in an array on a sheet.

Among such microneedles, there is one that is configured using a water soluble raw material such that it is dissolved by moisture existing within the skin, moisture given off by the skin, and the like. In addition, it is also possible to use moisture that exists in places other than the skin; for example, Patent Literature 1 (Japanese Unexamined Patent Application Publication No. 2011-194189) describes an example wherein a cosmetic liquid containing sheet is brought into contact with a transdermal patch from the side of the transdermal patch opposite that of the skin, and the moisture contained in the cosmetic liquid containing sheet is introduced to the microneedles.

A microneedle array in Patent Literature 1 is formed using an in vivo soluble substance, such as hyaluronic acid or a collagen, as a raw material. Here, an example is described wherein the microneedle array is formed using as a raw material a substance that dissolves in water in particular. Furthermore, to assemble the microneedle patch, an adhesive tape, which is made of polyethylene and from which the center portion has been cut out, is attached to the circumference of an elliptical substrate of the microneedle array of Patent Literature 1. This elliptical microneedle array has a long side that is approximately 30 mm and a short side that is approximately 20 mm.

In addition, Patent Literature 2 (Japanese Unexamined Patent Application Publication No. 2010-94414) describes a manufacturing method wherein a microneedle sheet is formed of a water soluble macromolecular substance, and a microneedle sheet solidified body is bonded to a support body sheet via an adhesive layer.

SUMMARY

As described above, in the microneedle patch described in Patent Literature 1, the cosmetic liquid containing sheet can directly contact the microneedle array, and consequently it is easy to supply moisture to the microneedles, which makes for a highly functional microneedle patch. However, in the microneedle patch described in Patent Literature 1, the microneedle array and the adhesive tape are adhered to one another over just a small area of the periphery of the microneedle array, and consequently the affixing strength is low and the bond tends to break.

Moreover, a microneedle sheet patch described in Patent Literature 2 is configured such that a dried microneedle sheet and a support body sheet are bonded by an adhesive layer, and the microneedle sheet and the support body sheet are removed from a forming mold. In addition, the forming mold is configured such that it also functions as a package. Thus, a microneedle patch manufacturing method described in Patent Literature 2 features high production efficiency.

However, the microneedle sheet patch of Patent Literature 2 has a structure wherein, if the moisture is externally supplied to the microneedle sheet as in Patent Literature 1, then not only does the support body sheet interfere with the supply of that moisture but the adhesive layer also interferes.

An object of the present invention is to provide, for a transdermal patch comprising water soluble microneedles, a low cost transdermal patch with good functionality and a method of manufacturing the same.

The following explains aspects of the present invention as technical solutions. These aspects can be arbitrarily combined as needed.

A transdermal patch manufacturing method according to one aspect of the present invention comprises: affixing a water soluble microneedle sheet in a microneedle sheet affixing process, wherein a plurality of water soluble microneedles are formed in an array, in a first area of a moisture permeable sheet capable of passing therethrough water vapor from skin and whereon a first adhesive layer for adhering to the skin is formed on a skin opposing surface side opposing the skin; and assembling the transdermal patch in an assembling process by attaching, onto an outer surface of the moisture permeable sheet on the side opposite the skin opposing surface using a second adhesive layer having an adhesive strength less than that of the first adhesive layer, a reinforcing film that integrally includes a water vapor barrier sheet and a removable portion around the water vapor barrier sheet, the water vapor barrier sheet blocking the passage of water vapor through at least the first area, and the removable portion being capable of separating from and peeling off the water vapor barrier sheet.

According to the transdermal patch manufacturing method configured in this manner, when the transdermal patch is being attached onto the skin, the moisture permeable sheet can be reinforced by the reinforcing film, and therefore the handling of the transdermal patch becomes easy. In addition, the water vapor given off by the skin becomes available to be used by the water vapor barrier sheet, and thereby moisture can be supplied to the microneedle sheet which can promote the dissolving of the microneedle sheet. Furthermore, after the transdermal patch has been stuck onto the skin, the removable portion can be separated from and simply peeled off the water vapor barrier sheet because the adhesive strength of the first adhesive layer is less than that of the second adhesive layer. The transdermal patch having the water vapor barrier sheet can be made by attaching the reinforcing film, and therefore production cost can be reduced by reducing the manufacturing time and effort.

A transdermal patch manufacturing method according to another aspect of the present invention comprises an applying process, a mounting process, a drying process, a peeling process, an assembling process, and an first adhesive layer forming process. In further detail, the transdermal patch manufacturing method according to this other aspect of the present invention comprises: applying, to a stamper having minute holes for forming microneedles, a raw materials aqueous solution of the microneedles in the applying process; bringing a moisture permeable sheet, which passes therethrough vapor of the raw materials aqueous solution, into contact with the applied raw materials aqueous solution, thereby mounting the moisture permeable sheet onto the raw materials aqueous solution and sandwiching the raw materials aqueous solution between the moisture permeable sheet and the stamper in the mounting process; evaporating at least some of the sandwiched raw materials aqueous solution that pass through the moisture permeable sheet and forming the microneedles by a dried body of the raw materials aqueous solution in the drying process, peeling the stamper from the microneedles formed in the drying process in the peeling process; assembling the transdermal patch in an assembling process by attaching a water vapor barrier sheet to an outer surface side of the moisture permeable sheet, which is the opposite a skin opposing surface, whereon the microneedles are fixed in the drying process and whereon a first adhesive layer for adhering to skin is to be formed, the water vapor barrier sheet blocking the passage of water vapor therethrough; and forming the first adhesive layer on the moisture permeable sheet in an a first adhesive layer forming process prior to the completion of the assembling process, by forming the first adhesive layer outside of a raw materials aqueous solution area of the moisture permeable sheet that is in contact with the raw materials aqueous solution.

According to the transdermal patch manufacturing method configured in this manner, in the drying process, the microneedles are formed by passing the water vapor through the moisture permeable sheet and consequently are dried in the state wherein the dried body of the raw materials aqueous solution is brought into direct contact with the moisture permeable sheet; thus, the dried body can be affixed to the moisture permeable sheet without the dried body and the moisture permeable sheet separating owing to the bonding agent layer. Consequently, because the bonding agent layer for adhering the microneedles to the moisture permeable sheet is omitted, it is easy to manufacture the transdermal patch such that it is easy to form thinly, and the transdermal patch is easy to attach onto the skin and is not conspicuous even when attached onto the skin. In addition, if moisture from the outer surface side of the moisture permeable sheet contacts the microneedles, then it is easy to make the moisture reach the microneedles because the distance from the moisture permeable sheet to the dried body is short, which makes it easy to manufacture the transdermal patch such that it is easy to impart moisture. Furthermore, in the peeling process, if the microneedles are peeled off the stamper, then the state obtains wherein the microneedles are adhered to the moisture permeable sheet and therefore the process of bonding the microneedles to the moisture permeable sheet is omitted, which improves productivity.

In the present transdermal patch manufacturing method, the moisture permeable sheet may comprise a fiber sheet or a plastic film, the plastic film having at least one of a plurality of vapor permeating holes each with a hole diameter of 0.1 μm to 100 μm, and a plurality of openings each with an opening diameter of equal to or greater than 0.5 mm and equal to or less than 4.5 mm. Thus, by using the plastic film having the vapor permeating holes, the openings, and the like, or the fiber sheet in the moisture permeable sheet, when the moisture permeable sheet is attached onto the skin, the water vapor from the skin can pass through. Thus, it is possible to manufacture the transdermal patch such that it does not get moist and to provide at low cost the transdermal patch such that it does not get moist.

In the present transdermal patch manufacturing method, the moisture permeable sheet may comprise a water absorbing layer made of a fiber sheet or a water absorbing layer containing water absorbing macromolecule, on a plastic film having at least one of a plurality of vapor permeating holes each with a hole diameter of 0.1 μm to 100 μm, and a plurality of openings each with an opening diameter of equal to 0.5 mm or greater than 0.5 mm and equal to or less than 4.5 mm; and in the microneedle sheet affixing process, the microneedle sheet contacting the water absorbing layer disposed in the first area may be affixed. Thereby, the microneedle sheet, which contacts the water absorbing layer in the first area, can be simply implemented, and the water absorbing layer that plays the role of, for example, water holding by the microneedle sheet, can be provided simply.

In the present transdermal patch manufacturing method, in the drying process, the moisture permeable sheet may be dried while being held flat. Thereby, when the moisture permeable sheet is being dried, it is possible to prevent the dried body of the raw materials aqueous solution from warping, and thereby to efficiently manufacture a transdermal patch comprising a flat moisture permeable sheet.

In the present transdermal patch manufacturing method the moisture permeable sheet may have a porous sheet base material that is formed by the application of the raw materials aqueous solution in a sheet shape to the moisture permeable sheet in advance and the porous sheet base material contacts the raw materials aqueous solution in the mounting process; and the drying process may include a process that forms the microneedles by drying the raw materials aqueous solution in the state where the sheet shaped base material has been brought into contact with the raw materials aqueous solution filling the minute hole. Thereby, during drying, the sheet shaped substrate that contacts the raw materials aqueous solution can be made to absorb the moisture from the raw materials aqueous solution, which makes it possible to increase the production speed.

In the present transdermal patch manufacturing method, the moisture permeable sheet comprises a water absorbing layer made of a fiber sheet or a water absorbing layer containing water absorbing macromolecule, on a plastic film having at least one of a plurality of vapor permeating holes each with a hole diameter of 0.1 μm to 100 μm, and a plurality of openings each with an opening diameter of equal to or greater than 0.5 mm and equal to or less than 4.5 mm, and the water absorbing layer contacts the raw materials aqueous solution in the mounting process; and the drying process includes a process that forms the microneedles by drying the raw materials aqueous solution in the state where the water absorbing layer has been brought into contact with the raw materials aqueous solution that has filled the minute holes. If configured in this manner, then, during drying, the water absorbing layer that contacts the raw materials aqueous solution can be made to absorb the moisture, which makes it possible to increase the production speed.

A transdermal patch according to one aspect of the present invention comprises a microneedle sheet, a moisture permeable sheet, and a water vapor barrier sheet. In further detail, the transdermal patch according to this one aspect comprises: the microneedle sheet having a water soluble sheet shaped substrate and a plurality of water soluble microneedles formed in an array on the substrate; the moisture permeable sheet passing therethrough water vapor and being made of a fiber sheet or a plastic film, the plastic film having at least one of vapor permeating holes each with a hole diameter of 0.1 μm to 100 μm and a plurality of openings each with an opening diameter of equal to or greater than 0.5 mm and equal to or less than 4.5 mm, the moisture permeable sheet having, wherein the microneedle sheet is affixed to a first area on a skin opposing surface side opposing a skin and having a first adhesive layer is applied to the skin opposing surface side; and the reinforcing film adhered, by a second adhesive layer having an adhesive strength less than that of the first adhesive layer, to an outer surface of the moisture permeable sheet, the outer surface being on the side opposite the skin opposing surface; wherein, the reinforcing film includes a water vapor barrier sheet, the water vapor barrier sheet blocking the passage of water vapor through at least the first area, and a removable portion around the water vapor barrier sheet being able to be separated from and able to be peeled off the water vapor barrier sheet.

According to the transdermal patch configured in this manner, when the transdermal patch is attached onto the skin, the water vapor that is given off by the skin and that passes through the gap between the microneedle sheet, and the vapor permeating holes of the moisture permeable sheet, the fiber, or the like is blocked by the water vapor barrier sheet. Consequently, the water vapor given off by the skin becomes available to be used by the water vapor barrier sheet, and thereby moisture can be supplied to the microneedle sheet which can promote the dissolving of the microneedle sheet. In addition, it is possible to prevent the moisture permeable sheet from deforming owing to the water vapor barrier sheet and to prevent the microneedle sheet which is affixed to the moisture permeable sheet from being peeled off owing to the deformation of the moisture permeable sheet. Furthermore, when the transdermal patch is being attached onto the skin, the moisture permeable sheet can be reinforced by the reinforcing film, and therefore the handling of the transdermal patch becomes easy. Furthermore, after the transdermal patch has been attached onto the skin, the removable portion can be separated from and simply peeled off the water vapor barrier sheet because the adhesive strength of the first adhesive layer is less than that of the second adhesive layer. Consequently, the convenience of the transdermal patch is improved during use.

In the present transdermal patch, the reinforcing film may be formed of a material having a loop stiffness value larger than that of the moisture permeable sheet. By configuring the transdermal patch in this manner, the reinforcing film maintains a shape such that the transdermal patch is easy to hold, which makes it possible to solve problems such as the moisture permeable sheet deforming, making the transdermal patch difficult to attach onto the skin.

The present transdermal patch may further comprise: a cover film that is adhered to the moisture permeable sheet by an adhesive agent and, together with the reinforcing film, forms a cavity that envelops the microneedle sheet such that the cover film does not contact the microneedle sheet. By configuring the transdermal patch in this manner, it is possible to prevent the microneedles from getting damaged by the cover film and the reinforcing film during handling of the transdermal patch, such as during transport, and thereby it is possible to prevent a reduction in the functionality of the transdermal patch caused by damage to the microneedles.

According to a transdermal patch and a transdermal patch manufacturing method of the present invention, it is possible to provide, at low cost, the transdermal patch in which it is easy to supply moisture to microneedles, the handling of the microneedles is easy, and the like.

DETAILED DESCRIPTION OF EMBODIMENTS

First Embodiment

Figure 2:
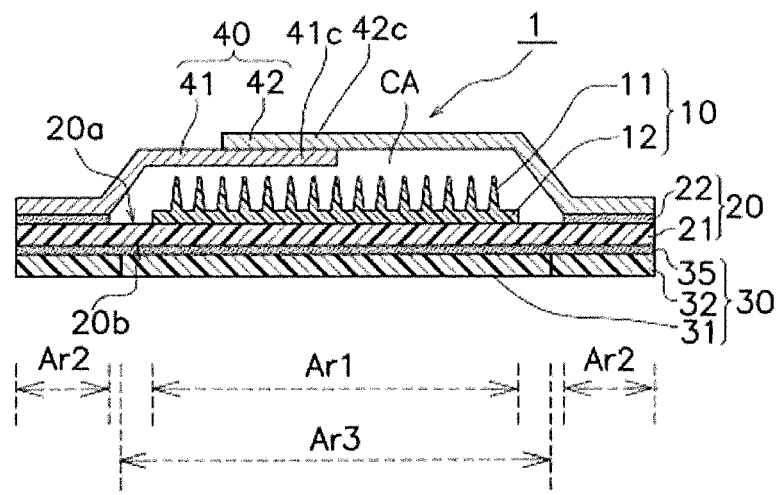
FIG. 2 is a schematic cross sectional view for explaining the structure of the transdermal patch illustrated in FIG. 1.
Figure 3:
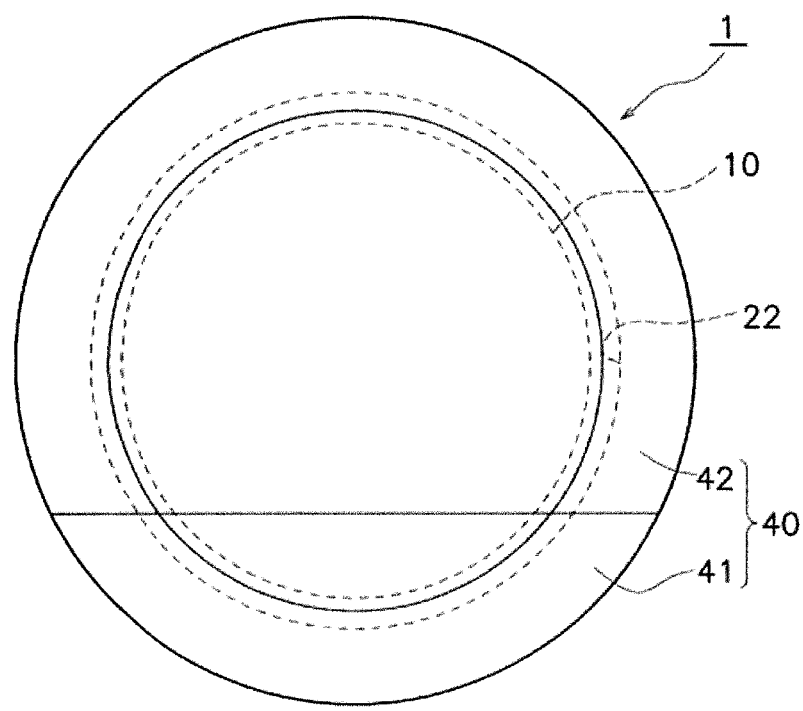
FIG. 3 is a schematic plan view for explaining the structure of the transdermal patch illustrated in FIG. 1.

Before explaining a method of manufacturing a transdermal patch according to a first embodiment of the present invention, the overall structure of the transdermal patch will be explained with reference to FIG. 1 through FIG. 3.

(1) Structure of Transdermal Patch

Figure 1:
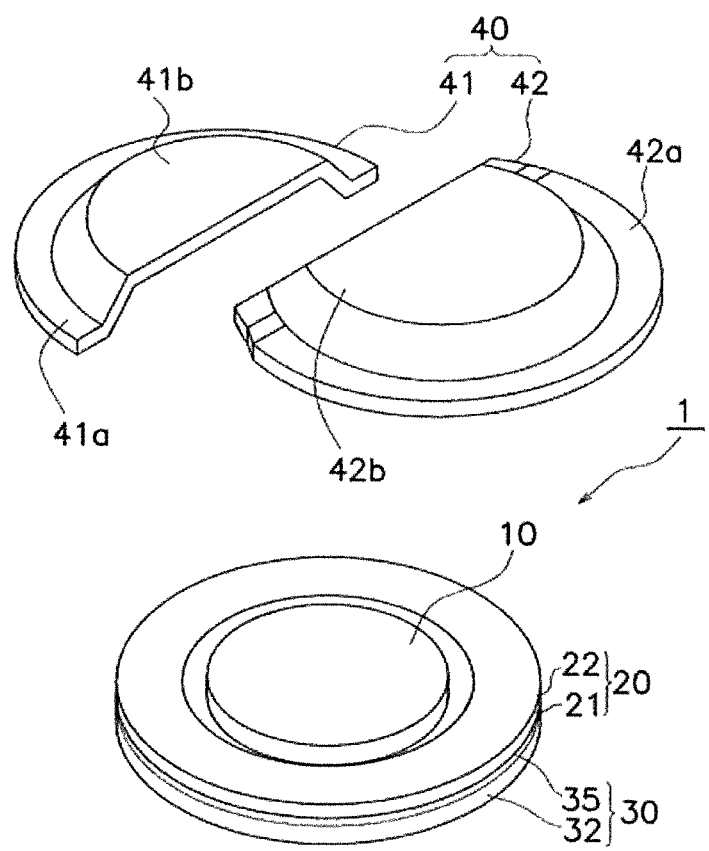
FIG. 1 is a schematic oblique view for explaining the structure of a transdermal patch according to a first embodiment.

FIG. 1 is an exploded oblique view of part of the transdermal patch according to the first embodiment. FIG. 2 illustrates a schematic cross sectional structure of the transdermal patch illustrated in FIG. 1, and FIG. 3 illustrates a schematic planar structure of the transdermal patch illustrated in FIG. 1.

As illustrated in FIG. 1, a transdermal patch 1 comprises a microneedle sheet 10, a moisture permeable sheet 20, a reinforcing film 30, and a cover film 40. The microneedle sheet 10 explained in the first embodiment has the shape of a disk of a size having a radius of approximately several millimeters to several tens of millimeters and a thickness of approximately several hundred micrometers.

(1-1) Microneedle Sheet

A drug or the like is administered by attaching on the microneedle sheet 10 such that it principally contacts a person's skin. In the microneedle sheet 10, microneedles 11 as illustrated in FIG. 2 are provided on a discoidal substrate 12, and the microneedles 11 are disposed in a portion, of the area on the substrate 12, that contacts the person's skin. The microneedles 11 penetrate into the skin, which promotes the administration of the drug or the like. Each of the microneedles 11 has, for example, a conical shape having a cone height of from 1 μm to 500 μm and a base cross sectional diameter:height ratio of from 1:1.5 to 1:5, thereby exhibiting a shape having a high aspect ratio (height/cross sectional diameter).

The microneedle sheet 10 comprises, as the principal materials, for example, a water soluble drug and a water soluble macromolecule, such as hyaluronic acid, a water soluble collagen, dextran, chondroitin sulfate, or the like, to which the drug has been added. Furthermore, the water soluble macromolecule to which the medicine is added is preferably an in vivo soluble water soluble macromolecule; in vivo soluble water soluble macromolecules, for example, can be a sodium salt of chondroitin, hyaluronic acid, and dextran.

The substrate 12 of the microneedle sheet 10 is affixed such that it directly contacts the moisture permeable sheet 20. The surface of the moisture permeable sheet 20 to which the substrate 12 is affixed is a skin opposing surface 20a, which opposes the skin; the area of the skin opposing surface 20a in which the substrate 12 is affixed is a first area Ar1.

(1-2) Moisture Permeable Sheet

The moisture permeable sheet 20 is formed of a polyurethane film 21 having numerous (a plurality of) vapor permeating holes (not shown), through which water vapor passes, having, for example, a hole diameter of 0.1 μm to 100 μm, and preferably 10 μm to 30 μm. The thickness of the moisture permeable sheet 20 is, for example, approximately several tens of microns. In addition, in the moisture permeable sheet 20, an adhesive layer 22 for attaching to the skin is provided on the skin opposing surface 20a. The adhesive layer 22 is formed into a circular ring shape such that it surrounds the circumference of the discoidal substrate 12. The moisture permeable sheet 20 is configured to pass water vapor through the adhesive layer 22 and the vapor permeating holes of the polyurethane film 21 such that the skin does not become sweaty at the location at which the moisture permeable sheet 20 is attached on. Consequently, for example, the adhesive layer 22 is sparsely applied such that the application surface area is small so that the adhesive layer 22 does not block all the vapor permeating holes. The adhesive layer 22 is formed in a second area Ar1 of the area outside of the first area Ar1 of the skin opposing surface 20a of the moisture permeable sheet 20.

The reinforcing film 30 is adhered to an outer surface 20b on the side of the moisture permeable sheet 20 opposite the skin opposing surface 20a. The reinforcing film 30 comprises an adhesive layer 35 and is attached onto the moisture permeable sheet 20 via the adhesive layer 35. When the reinforcing film 30 is peeled off the moisture permeable sheet 20, the adhesive layer 35 is peeled off the moisture permeable sheet 20 and stays with the reinforcing film 30. The reinforcing film 30 is formed of a plastic film, such as polypropylene, polyethylene, or polyester, and has sufficient water vapor barrier characteristics compared with the polyurethane film 21 because the plastic with which the reinforcing film 30 is formed does not have vapor permeating holes like the polyurethane film 21 does.

(1-3) Reinforcing Film

Figure 10:
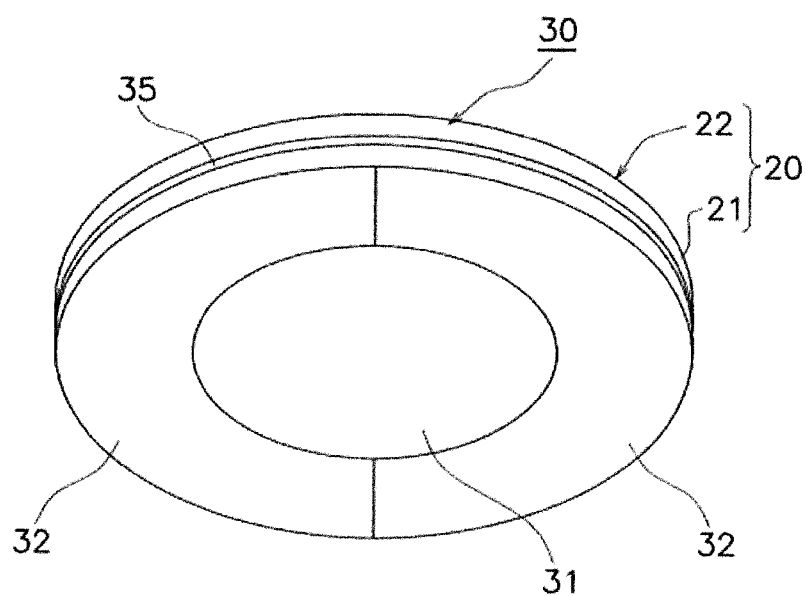
FIG. 10 is a schematic cross sectional view for explaining the assembling process according to the first embodiment.

FIG. 10 is an oblique view, viewed from the reinforcing film 30 side, of the transdermal patch 1 after the reinforcing film 30 has been adhered. The thickness of the reinforcing film 30 is, for example, approximately ten-odd micrometers to several hundred micrometers. The reinforcing film 30 comprises a water vapor barrier sheet 31 and a removable portion 32, which is integrally formed with the water vapor barrier sheet 31. For example, the water vapor barrier sheet 31 and the removable portion 32 can be integrally formed by making a cut (a groove for cutting) or a separating line, such as perforations, in the plastic film, thereby making the configuration such that the removable portion 32 can be detached. The water vapor barrier sheet 31 is disposed in a portion that overlaps the third area Ar3. The third area Ar3 includes the area Ar1 and the area around the first area Ar1. The microneedle sheet 10 is affixed in the first area Ar1. The third area Ar3 is an area that includes the first area Ar1 and the area around it. Furthermore, the third area Ar3 may include part of the second area Ar2.

The removable portion 32 is removed during use. At that time, the adhesive layer 35, which is applied to the removable portion 32, is removed together with the removable portion 32. Consequently, during use, when the removable portion 32 is removed, the outer surface 20b of the moisture permeable sheet 20 is exposed to the atmosphere, and therefore does not become moist.

When the transdermal patch 1 is to be attached onto the skin and used, the transdermal patch 1 is attached onto the skin, after which the removable portion 32 alone is removed. To ensure that the moisture permeable sheet 20 does not peel off at that time, the composition, the thickness, the application surface area, and the like of the adhesive layers 22, 35 are adjusted such that the adhesive strength of the adhesive layer 35 is lower than that of the adhesive layer 22.

To improve the handling characteristic of the transdermal patch 1, the reinforcing film 30 is composed of a material that is firmer than the moisture permeable sheet 20. The firmness of the moisture permeable sheet 20 and that of the reinforcing film 30 are compared using values measured with a product named "loop stiffness tester" that is made by Toyo Seiki Seisaku-sho, Ltd., and the value of the reinforcing film 30 measured by the loop stiffness tester is set larger. For example, if the firmness of the moisture permeable sheet 20 is 0 mN/20 mm, then the firmness of the reinforcing film 30 is set to any value between 1 mN/15 mm and 1 N/15 mm. That is, if just the moisture permeable sheet 20, which is configured such that it deforms easily in order to closely follow deformation of the skin, is pinched by fingers, then the moisture permeable sheet 20 will adversely hang down owing to gravity, and therefore the microneedle sheet 10 will not readily attach to the desired location. Incidentally, if the reinforcing film 30 is adhered to the moisture permeable sheet 20, then, even if the reinforcing film 30 and the moisture permeable sheet 20 are pinched by fingers, the deformation of the reinforcing film 30 and the moisture permeable sheet 20 can be reduced to a degree such that they bend just a little bit, and therefore it becomes easy to attach the microneedle sheet 10 to the desired location.

(1-4) Cover Film

Given that the principal material of the microneedles 11 of the microneedle sheet 10 is a water soluble macromolecule as described above, the transdermal patch 1 comprises a cover film 40 to protect the microneedles 11 from breaking during transport and the like. Consequently, the cover film 40 has hardness, stiffness, and the like to a degree such that it does not deform even if, for example, multiple transdermal patches 1 strike one another during transport. When the transdermal patch 1 is used on a person's skin, the cover film 40 is peeled to expose the microneedle sheet 10, as illustrated in FIG. 1.

The cover film 40 comprises a lower side cover film 41 and an upper side cover film 42. The lower side cover film 41 and the upper side cover film 42 have flange parts 41a, 42a, respectively, each of which adheres to the adhesive layer 22. In the cover film 40, a dome shaped portion, which protrudes toward the outer side, is formed on an inner circumferential side of the flange parts 41a, 42a. To form the dome shaped portion of the cover film 40, the lower side cover film 41 and the upper side cover film 42 comprise dome parts 41b, 42b, respectively. Together with the reinforcing film 30, the dome parts 41b, 42b form a cavity CA (refer to FIG. 2), which is a space for storing the microneedle sheet 10. Owing to the cavity CA, the microneedles 11 are configured such that they do not touch other portions, such as the cover film 40. In addition, in the cover film 40, the lower side cover film 41 and the upper side cover film 42 have overlapping portions 41c, 42c, at which the lower side cover film 41 and the upper side cover film 42 overlap one another, so that a gap is not formed between the lower side cover film 41 and the upper side cover film 42.

(2) Transdermal Patch Manufacturing Method

Next, the transdermal patch manufacturing method according to the first embodiment will be explained, with reference to FIG. 4 through FIG. 10.

(2-1) Adhesive Layer Forming Process

Figure 4:
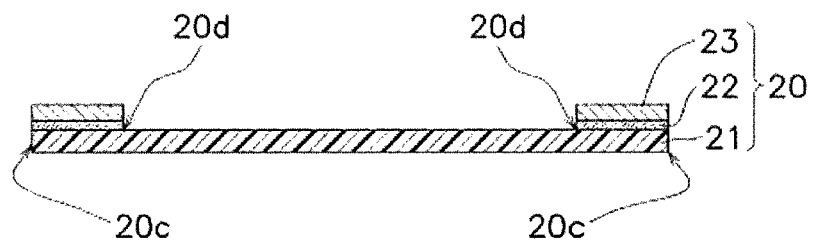
FIG. 4 is a schematic cross sectional view of a moisture permeable sheet used in the first embodiment.

FIG. 4 illustrates a process, which is one example of an adhesive layer forming process, wherein the moisture permeable sheet 20 including an adhesive agent is prepared. The moisture permeable sheet 20 illustrated in FIG. 4 appears circular in a plan view, as illustrated in FIG. 3. The adhesive agent is applied in a ring shape only between an outer circumference 20c and an inner circumference 20d, which has a radius smaller than that of the outer circumference 20c, of the polyurethane film 21, and thereby the adhesive layer 22 is formed. In other words, the adhesive layer 22 is not formed in the area on the inner side of the inner circumference 20d of the moisture permeable sheet 20.

A peelable sheet 23 is adhered onto the adhesive layer 22 of the moisture permeable sheet 20. The peelable sheet 23 plays the role of ensuring that waste, dust, and the like does not reach the adhesive layer 22 during manufacture.

The present example of the manufacturing method described, as the adhesive layer forming process, a case wherein the moisture permeable sheet 20, to which the adhesive layer 22 has been applied in advance, is prepared, but the adhesive layer forming process may be formed any time before an assembling process, which is described below, is completed. For example, the manufacturing process may proceed using a moisture permeable sheet to which the adhesive layer 22 has not been applied, and the adhesive layer 22 may be formed any time before the assembling process is completed.

(2-2) Applying Process

Figure 5A:
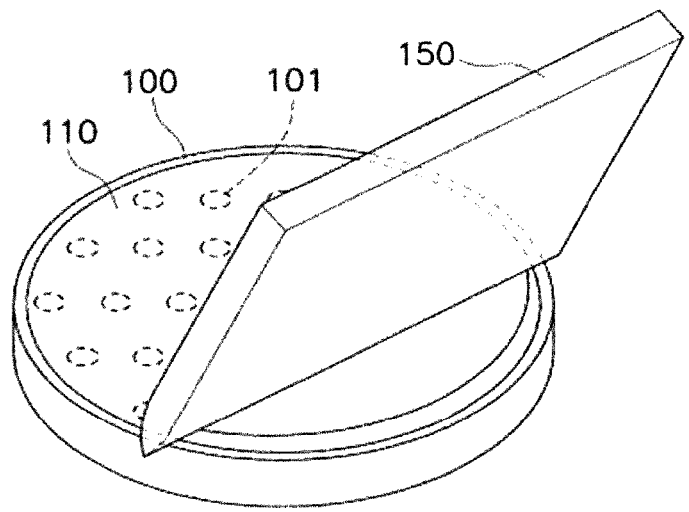
FIG. 5A is a schematic oblique view for explaining an applying process according to the first embodiment.
Figure 5B:
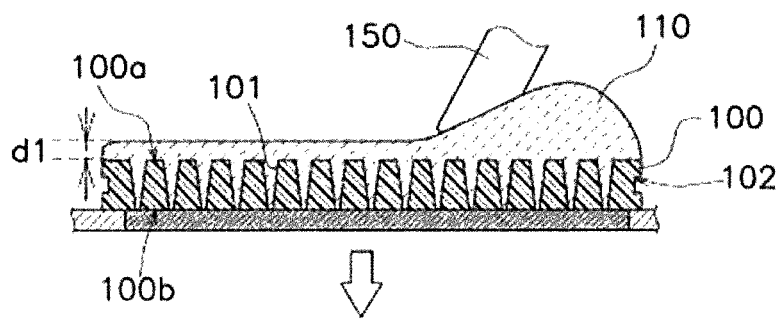
FIG. 5B is a schematic cross sectional view for explaining the same applying process.

An applying process in which a raw materials aqueous solution 110 is applied to a stamper 100 will now be explained, with reference to FIGS. 5A and 5B. FIG. 5A illustrates a state wherein the stamper, to which the raw materials aqueous solution has been applied, is viewed obliquely, and FIG. 5B illustrates a state of a cross section of the stamper to which the raw materials aqueous solution has been applied. As illustrated in FIG. 5A, the raw materials aqueous solution 110 is applied by a squeegee 150 such that the raw materials aqueous solution 110 has a constant thickness dl relative to a front surface 100a of the stamper 100. On that account, a tip of the squeegee 150 moves horizontally with respect to the front surface 100a of the stamper 100. At this time, the raw materials aqueous solution 110 also fills micro through holes 101 in the stamper 100. The stamper 100 may be formed of a resin, such as polyethylene or fluororesin, and in particular may be formed of a thermoplastic resin. Once it is used up, the stamper 100 is hygienically managed by, for example, being recycled back into raw materials.

If each micro through hole 101 has, for example, a conical shape, then it is approximately several tens of micrometers to several hundred micrometers at the front surface 100a of the stamper 100 and is approximately several to ten-odd micrometers at a rear surface 100b of the stamper 100. Thus, because the micro through holes 101 are extremely small, the raw materials aqueous solution 110 cannot sufficiently fill the micro through holes 101 merely by being forced in from the front surface using the squeegee 150. Accordingly, it is preferable, for example, to set the gas pressure on the rear surface 100b side of the stamper 100 greater than the atmospheric pressure on the front surface 100a side of the stamper 100, that is, it is preferable to perform suction from the rear surface 100b side and thereby to fill the micro through holes 101 completely with the raw materials aqueous solution 110. Furthermore, it is further preferable to apply pressure such that the raw materials aqueous solution 110 is forced into the micro through holes 101 when the pressure on the front surface 100a side of the stamper 100 is increased such that it is higher than atmospheric pressure during and/or after the application of the raw materials aqueous solution 110.

(2-3) Mounting Process

Figure 6:
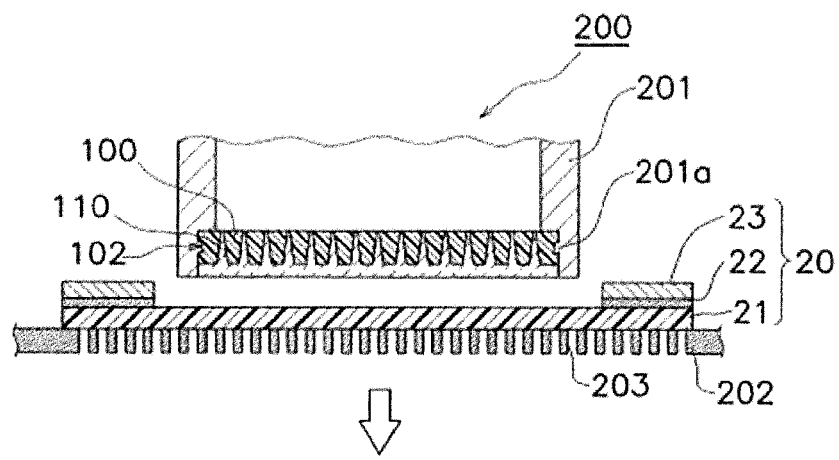
FIG. 6 is a schematic cross sectional view for explaining a mounting process according to the first embodiment.

FIG. 6 illustrates a cross section of the moisture permeable sheet 20 and the stamper 100 in the mounting process. In the stamper 100, which has been coated with the raw materials aqueous solution 110, for example, a mating part 102 is mated to an arm 201 of a manufacturing apparatus 200 and thereby the stamper 100 is moved with respect to the moisture permeable sheet 20 with good accuracy. The arm 201 is, for example, a circular cylindrical component having a rib 201a that mates with the mating part 102, and the arm 201 is configured such that it is vertically split in half and sandwiches the stamper 100 from the left and the right. Furthermore, the stamper 100 is mounted to the moisture permeable sheet 20 with the front surface 100a side of the stamper 100 facing the moisture permeable sheet 20. Because the position of the moisture permeable sheet 20 relative to the arm 201 must be decided when the stamper 100 is mounted, the moisture permeable sheet 20 is vacuum chucked to a pedestal 202 and thereby fixed onto the manufacturing apparatus 200. On that account, the pedestal 202 is provided with numerous suction holes 203, and the pressure inside the suction holes 203 is lower than atmospheric pressure. The arrow in FIG. 6 is a symbol that conceptually indicates this suction. The position at which the stamper 100 is mounted is the inner side of the inner circumference 20d of the moisture permeable sheet 20. When mounting, the stamper 100 is mounted to the moisture permeable sheet 20 such that bubbles do not enter the space between the raw materials aqueous solution 110 and the moisture permeable sheet 20. To perform the mounting in this manner, it is acceptable to press the stamper 100 against the moisture permeable sheet 20 such that the raw materials aqueous solution 110 oozes out a bit from the stamper 100.

(2-4) Drying Process

Figure 7A:
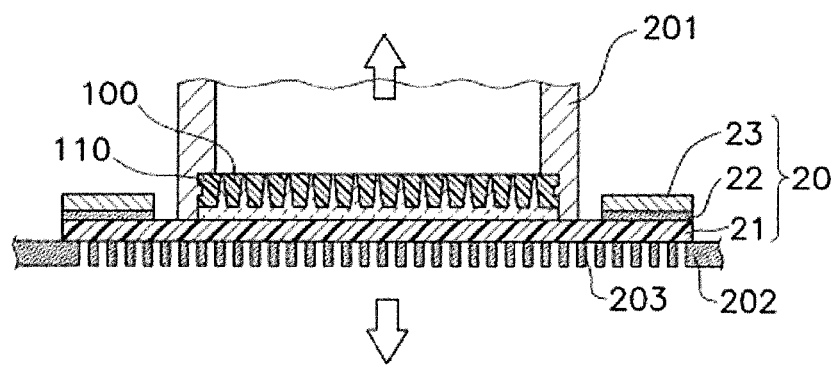
FIG. 7A is a schematic cross sectional view for explaining a state before the drying of a drying process according to the first embodiment.
Figure 7B:
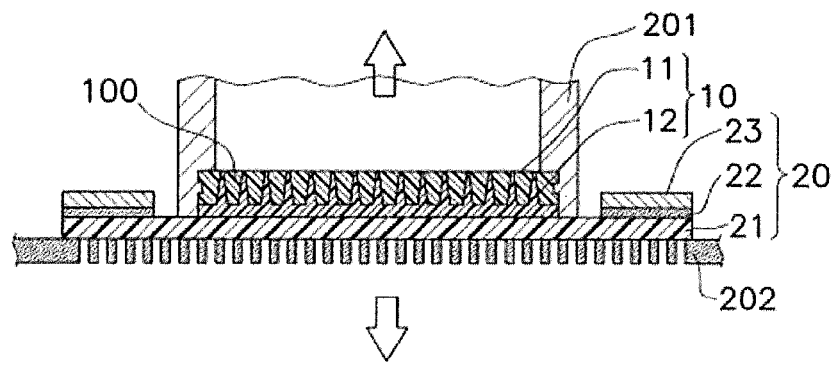
FIG. 7B is a schematic cross sectional view for explaining a state after the drying of the drying process.

FIG. 7A illustrates a cross section of the moisture permeable sheet 20 and the stamper 100 prior to the drying of the drying process, and FIG. 7B illustrates a cross section of the moisture permeable sheet 20 and the stamper 100 after the drying of the drying process. As illustrated in FIG. 7A, the raw materials aqueous solution 110 exists in the moisture permeable sheet 20, to which the stamper 100 has been mounted, such that the raw materials aqueous solution 110 is interposed between the stamper 100 and the moisture permeable sheet 20. The stamper 100 is made of, for example, a resin, and its permeability with respect to water vapor is poor. In contrast, because numerous vapor permeating holes (not shown), each of which has a hole diameter of 0.1 μm to 100 μm, exist in the moisture permeable sheet 20, the moisture permeable sheet 20 passes vapor well. Consequently, the drying of the raw materials aqueous solution 110 is performed by expelling the water vapor to an outer part via the moisture permeable sheet 20. To assist this drying, the outer surface 20b side of the moisture permeable sheet 20 is, continuing from the mounting process, maintained at a pressure lower than atmospheric pressure. To promote drying, it is preferable to evacuate the suction holes 203 using a vacuum pump or the like. In addition, the arm 201 side, too, is preferably adjusted to the same pressure as the suction holes 203 to ensure that the raw materials aqueous solution 110 is not sucked into the suction holes 203. Such a pressure state is indicated by the arrow symbols in FIG. 7A and FIG. 7B.

When the drying of the raw materials aqueous solution 110 progresses, the microneedle sheet 10 is formed between the moisture permeable sheet 20 and the stamper 100, as illustrated in FIG. 7B.

(2-5) Peeling Process

Figure 8:
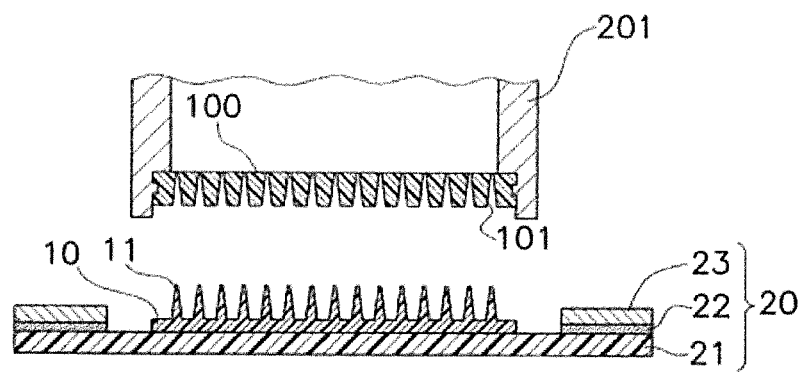
FIG. 8 is a schematic cross sectional view for explaining a peeling process according to the first embodiment.

FIG. 8 illustrates a peeling process in which the stamper 100 is peeled from the moisture permeable sheet 20. In the peeling process, in the state wherein the moisture permeable sheet 20 is vacuum chucked to the pedestal 202, the stamper 100 is gently lifted off the moisture permeable sheet 20. Thereby, the microneedles 11 separate from the micro through holes 101 of the stamper 100, and the microneedle sheet 10 having the microneedles 11 is formed such that the microneedle sheet 10 directly contacts and is affixed to the moisture permeable sheet 20. At this time, a pressure higher than atmosphere pressure may be applied from the rear surface 100b side of the stamper 100 so that the microneedles 11 easily separate from the stamper 100.

(2-6) Assembling Process

Figure 9:
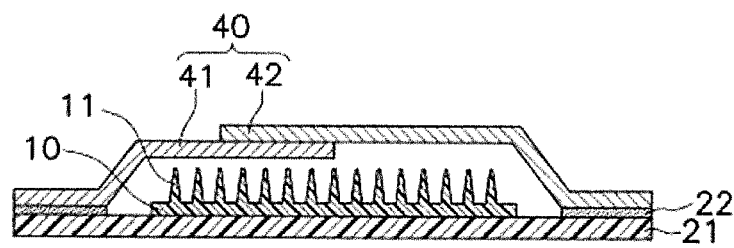
FIG. 9 is a schematic cross sectional view for explaining an assembling process according to the first embodiment.

FIG. 9 and FIG. 10 illustrate states wherein the assembly of the transdermal patch being assembled in the assembling process is in progress and is complete, respectively. FIG. 9 illustrates a state wherein the cover film 40 is adhered to the moisture permeable sheet 20 illustrated in FIG. 8. To attach the cover film 40 onto the polyurethane film 21, the peelable sheet 23 is peeled off. Furthermore, first, the lower side cover film 41 is adhered to the adhesive layer 22 and, next, the upper side cover film 42 is adhered. The lower side cover film 41 and the upper side cover film 42 are adhered such that the overlapping portions 41c, 42c overlap one another.

After the cover film 40 is adhered, the reinforcing film 30 is adhered. The reinforcing film 30 is configured such that it is removed by the removable portion 32 during use; however, in the assembling process, the reinforcing film 30 is adhered in the state wherein the water vapor barrier sheet 31 and the removable portion 32 have been integrated. On that account, the reinforcing film 30 comprises the adhesive layer 35. As illustrated in FIG. 10, when the completed transdermal patch 1 is viewed obliquely from below, the adhered reinforcing film 30 is visible.

The transdermal patch 1 manufactured in this manner is stored in, for example, a bag laminated with aluminum or the like such that water vapor can be blocked, and is managed such that the microneedle sheet 10 does not draw in moisture before beginning to use. In addition, when the transdermal patch 1 is delivered to a consumer, the transdermal patch 1 is handled in a state in which it is stored in a bag that can block such water vapor.

Second Embodiment (3) Transdermal Patch Manufacturing Method

Figure 11A:
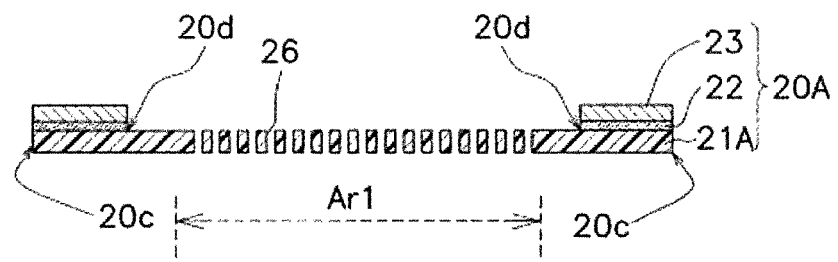
FIG. 11A is a schematic cross sectional view of the moisture permeable sheet used in a second embodiment.

Next, the transdermal patch manufacturing method according to a second embodiment will be explained, with reference to FIG. through FIG. 14. The transdermal patch manufacturing method according to the second embodiment differs from the transdermal patch manufacturing method according to the first embodiment in that numerous openings 26, each having an opening diameter of 0.5 mm or more, and less than 4.5 mm, are formed in a porous sheet base material film 21A of a moisture permeable sheet 20A, as illustrated in FIG. 11A. Other aspects are the same as those in the first embodiment, and consequently identical constituent parts are assigned the same symbols and explanations thereof are omitted where appropriate.

Figure 11B:
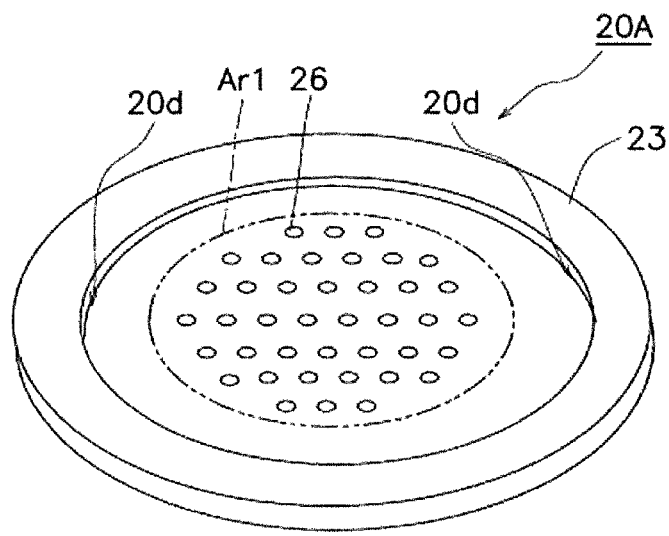
FIG. 11B is a schematic oblique view of the moisture permeable sheet used in the second embodiment.

As illustrated in FIG. 11B, the openings 26 are formed with a staggered arrangement in the polyurethane film 21A of the moisture permeable sheet 20A. The diameter of the openings 26 is preferably 0.5 mm or greater and less than 4.5 mm. The occupancy percentage of the openings 46 per unit of area is preferably 20% to 65%. If the diameter of the openings 26 is smaller than 0.5 mm, then water permeability becomes poor, and if the diameter is larger than 4.5 mm, then it becomes difficult to obtain the required surface area of the adhesive surface. In addition, if the occupancy percentage of the openings 26 is less than 20%, then water does not pass through sufficiently, and if the occupancy percentage is 65% or greater, then sufficient adhesive strength cannot be obtained.

The area in which the openings 26 are formed is the first area Ar1, wherein the microneedle sheet 10 (refer to FIG. 13) is affixed. The aggregate surface area of the openings 26 occupying the first area Ar1 ranges from 20% to 65% of the surface area of the first area Ar1.

For the polyurethane film 21A, it is preferable to use a film having vapor permeating holes of 0.1 μm to 100 μm, as in the first embodiment. Thereby, it is possible to prevent the skin from becoming sweaty in the area in which the adhesive layer 22 is formed.

In the following mounting process, too, the second embodiment differs from the first embodiment only in that the moisture permeable sheet 20A is used.

Figure 12:
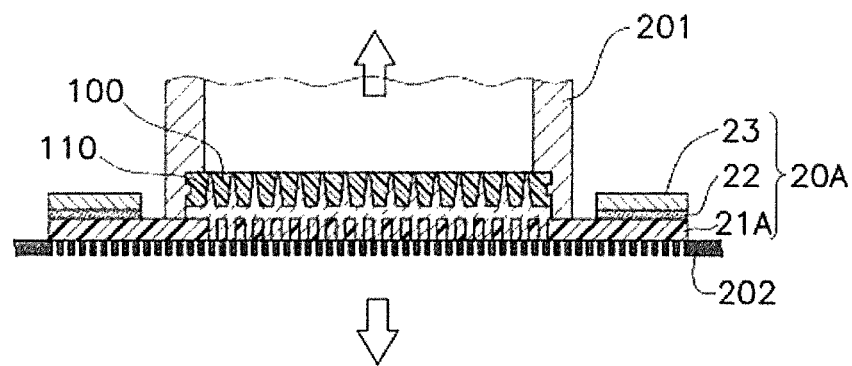
FIG. 12 is a schematic cross sectional view for explaining the drying process according to the second embodiment.

FIG. 12 illustrates the drying process according to the second embodiment. The drying process likewise is the same as the drying process of the first embodiment that was explained with reference to FIGS. 7A and 7B, and therefore a detailed explanation thereof is omitted. However, in the drying process according to the second embodiment, the openings 26 exist in the moisture permeable sheet 20A, and therefore the raw materials aqueous solution 110 easily flows out to the pedestal 202. Consequently, the same as in the first embodiment, it is preferable to set the pressure on the front surface 100a side and the pressure on the rear surface 100b side to be the same pressure. In addition, the diameter of the suction holes 203 of the pedestal 202 is preferably set smaller in the second embodiment. Consequently, the pedestal 202 can also be configured using, for example, a porous material. A large amount of moisture evaporates from the openings 26, and therefore the drying time of the drying process according to the second embodiment can be shortened as compared with the first embodiment. In addition, if the polyurethane film 21A also has vapor permeating holes of 0.1 μm to 100 μm, then drying becomes even easier.

In this drying process, the raw materials aqueous solution enters the openings 26 and solidifies, and the affixing strength between the microneedle sheet 10 and the moisture permeable sheet 20A increases more than that between the microneedle sheet 10 and the moisture permeable sheet 20 owing to the anchoring effect.

Figure 13:
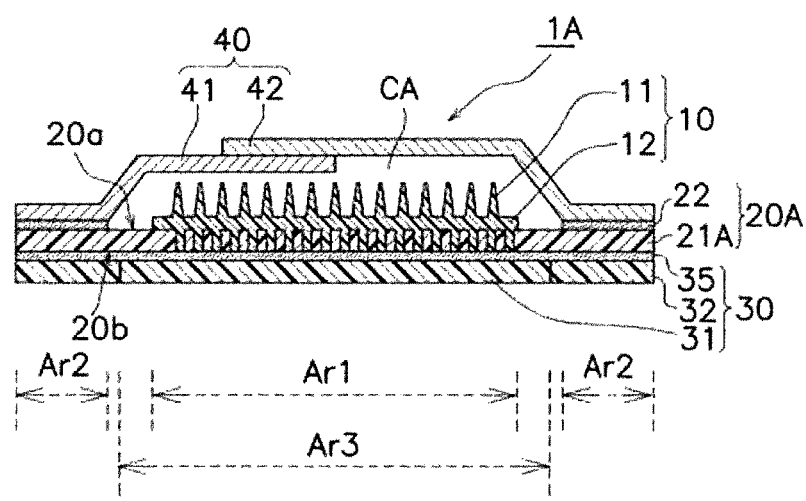
FIG. 13 is a schematic cross sectional view for explaining the structure of the transdermal patch according to the second embodiment.

FIG. 13 illustrates a cross sectional structure of a transdermal patch 1A after the assembling process according to the second embodiment. As can be understood by comparing FIG. 13 with FIG. 2, FIG. 10, and the like, except for the difference between the moisture permeable sheets 20, 20A, there are no differences between the transdermal patch 1A of the second embodiment and the transdermal patch 1 of the first embodiment with respect to their configurations.

Third Embodiment (4) Transdermal Patch Manufacturing Method

Next, the transdermal patch manufacturing method according to a third embodiment will be explained, with reference to FIG. 14 and FIG. 15. The transdermal patch manufacturing method according to the third embodiment differs from the transdermal patch manufacturing method according to the first embodiment in that, as illustrated in FIG. 14, adhesive coated portions 22a are discretely formed in the first area Ar1, in which the microneedle sheet 10 is affixed, of the polyurethane film 21 of a moisture permeable sheet 20B of the third embodiment. Other aspects are the same as those in the first embodiment; consequently, identical constituent parts are assigned the same symbols and explanations thereof are omitted where appropriate.

Figure 14:
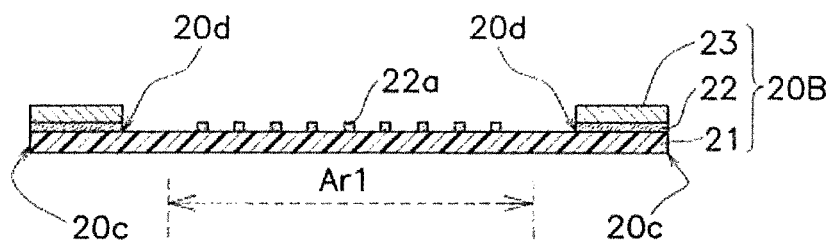
FIG. 14 is a schematic cross sectional view of the moisture permeable sheet used in a third embodiment.

In the polyurethane film 21 of the moisture permeable sheet 20B illustrated in FIG. 14, the adhesive coated portions 22a, which exist discretely in an island formation, are formed in the first area Ar1. Because the adhesive coated portions 22a exist discretely, in the drying process, the same as in the first embodiment, the raw materials aqueous solution 110 (refer to FIGS. 6, 7A and 7B) can be dried by passing the water vapor through the polyurethane film 21 at the portion of the first area Ar1 where there is no adhesive agent and evaporating the water vapor.

Figure 15:
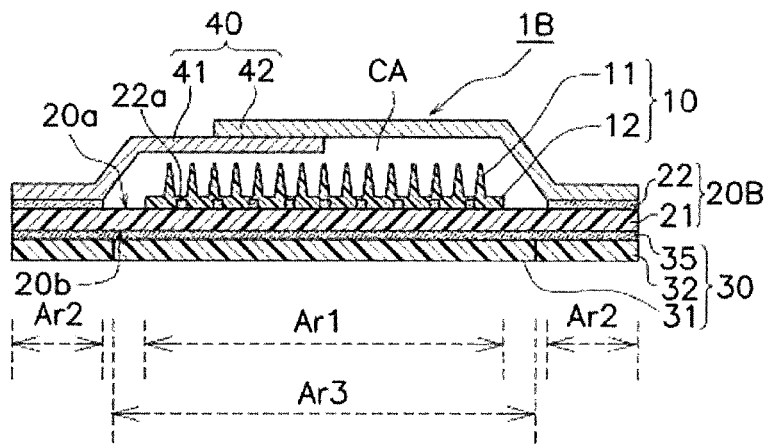
FIG. 15 is a schematic cross sectional view for explaining the structure of the transdermal patch according to the third embodiment.

FIG. 15 illustrates a cross sectional structure of a transdermal patch 1B after the assembling process according to the third embodiment. As can be understood by comparing FIG. 15 with FIG. 2, FIG. 10, and the like, there are no differences other than the difference in the moisture permeable sheets 20, 20B. In the transdermal patch 1B illustrated in FIG. 15, the adhesive coated portions 22a exist, even though partially, in the first area Ar1 between the microneedle sheet 10 and the moisture permeable sheet 20, and consequently the affixing strength of the microneedle sheet 10 with respect to the moisture permeable sheet 20B can be increased more than in the case of the transdermal patch 1 according to the first embodiment.

Fourth Embodiment (5) Transdermal Patch Manufacturing Method of Fourth Embodiment Next, the transdermal patch manufacturing method according to a fourth embodiment will be explained, with reference to FIG. 16. The transdermal patch manufacturing method according to the fourth embodiment differs from the transdermal patch manufacturing method according to the first embodiment in that a water absorbing sheet 27, which has air permeability over a wider area than the third area Ar3 wherein the water vapor barrier sheet 31 is affixed, is provided on a polyurethane film 21C of a moisture permeable sheet 20C illustrated in FIG. 16, and in that vents 28, which pass through the polyurethane film 21C and reach the water absorbing sheet 27, are provided. The water absorbing sheet 27 is formed of, for example, a fiber sheet, a water absorbing macromolecular sponge sheet, or the like. Other aspects of the configuration of a transdermal patch 1C according to the fourth embodiment are the same as those of the first embodiment, and consequently identical constituent parts are assigned the same symbols and explanations thereof are omitted where appropriate.

Figure 16:
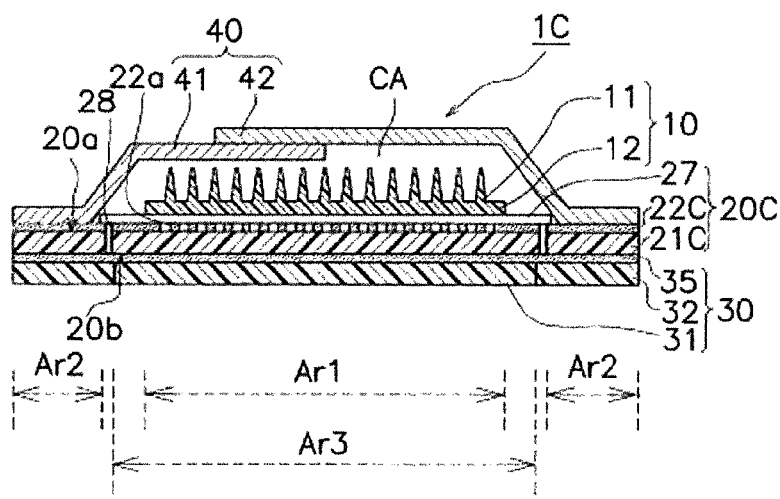
FIG. 16 is a schematic cross sectional view for explaining the structure of the transdermal patch according to a fourth embodiment.

FIG. 16 illustrates a cross sectional structure of the transdermal patch 1C after the assembling process according to the fourth embodiment. In the polyurethane film 21C of the moisture permeable sheet 20C illustrated in FIG. 16, the vents 28 are provided on the outer side of the third area Ar3. The vents 28 reach the water absorbing sheet 27, and the moisture adsorbed by the water absorbing sheet 27 can be sucked in or discharged through the vents 28. The water absorbing sheet 27 is adhered to the polyurethane film 21C by the discretely disposed adhesive coated portions 22a. Consequently, in the drying process, the water vapor can be discharged to the outer part by being passed through the vents 28 via the water absorbing sheet 27, which has air permeability, or through the adhesive layer 22 and the vapor permeating holes of the polyurethane film 21C.

Moreover, during use, the water vapor given off by the skin is blocked by the water vapor barrier sheet 31 and thereby can be introduced to the microneedle sheet 10. Furthermore, when it is desired to supply a large amount of moisture to the microneedle sheet 10, it is also possible to supply water to the water absorbing sheet 27 via the vents 28. The water absorbing sheet 27 comprises a fiber sheet, a water absorbing macromolecular sponge sheet, or the like, and therefore has a high water holding characteristic. Consequently, when it is desired to supply moisture to the microneedle sheet 10 over a comparatively long period of time, it is convenient if moisture is supplied using the water absorbing sheet 27.

Fifth Embodiment (6) Transdermal Patch Manufacturing Method of Fifth Embodiment

Next, the transdermal patch manufacturing method according to a fifth embodiment will be explained, with reference to FIG. 17. The transdermal patch manufacturing method according to the fifth embodiment differs from the transdermal patch manufacturing method according to the second embodiment in that a moisture permeable sheet 20D illustrated in FIG. 17 has a porous sheet shaped base material 29 in the first area Ar1 in which the microneedle sheet 10 is affixed. Other aspects are the same as those in the second embodiment; consequently, identical constituent parts are assigned the same symbols and explanations thereof are omitted where appropriate.

Figure 17:
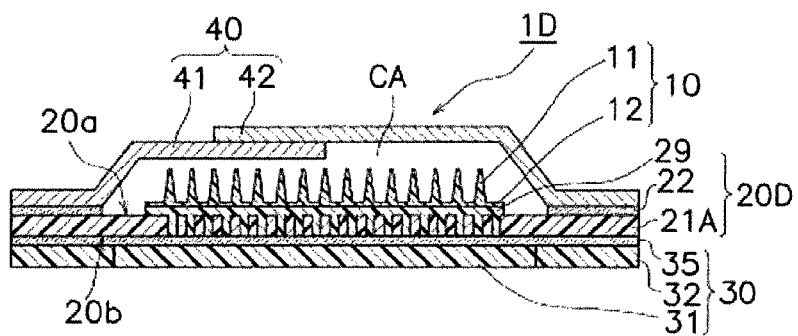
FIG. 17 is a schematic cross sectional view for explaining the structure of the transdermal patch according to a fifth embodiment.

FIG. 17 illustrates a cross sectional structure of a transdermal patch 1D after the assembling process according to the fifth embodiment. As in the second embodiment, the numerous openings 26 are provided in the polyurethane film 21A of the moisture permeable sheet 20D illustrated in FIG. 17.

The moisture permeable sheet 20D has a sheet shaped base material 29, which is formed by directly applying the raw materials aqueous solution to the first area Ar1 in advance and then drying such.

The sheet shaped base material 29 is porous and possesses numerous through holes that extend from the front surface of the sheet shaped base material 29 to the skin opposing surface 20a of the moisture permeable sheet 20D or the outer surface 20b side of the moisture permeable sheet 20D within the openings 26. The porous sheet base material 29 of this type can be made using, for example, a freeze drying manufacturing method (vacuum freeze drying method). Alternatively, the porous sheet base material 29 can also be made by drying the raw materials aqueous solution on the polyurethane film 21A in the shape of a sheet and then forming, by machining such as press molding, numerous through holes that pass through to the polyurethane film 21A.

In the mounting process, the stamper 100 (refer to FIG. 12) is mounted on the sheet shaped base material 29. Consequently, it results in the raw materials aqueous solution 110 being sandwiched between the stamper 100 and the sheet shaped base material 29. That is, it results in a state results where the microneedle sheet 10 illustrated in FIG. 17 is replaced by the raw materials aqueous solution 110 before drying.

In the drying process, the sheet shaped base material 29 is already dried, and consequently drying is promoted because the moisture in the raw materials aqueous solution 110 is absorbed by the sheet shaped base material 29. In addition, even though some of the holes of the sheet shaped base material 29 close up during drying, the water holding characteristic increases owing to the porosity, and consequently it becomes easy to stably supply moisture to the microneedle sheet 10.

Sixth Embodiment

Figure 18:
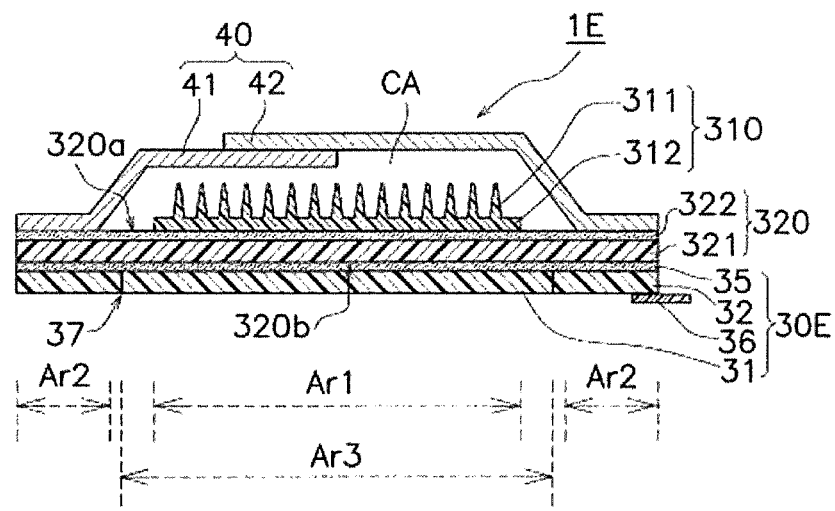
FIG. 18 is a schematic cross sectional view that illustrates one example of a cross sectional structure of the transdermal patch according to a sixth embodiment.

The first through fifth embodiments described above explained the case wherein neither an adhesive layer nor a bonding agent layer exists between the polyurethane film 21, 21A, 21C of the moisture permeable sheet 20, 20A, 20B, 20C, 20D and the microneedle sheet 10; however, as illustrated in FIG. 18, an adhesive layer 322 may be formed between a polyurethane film 321 of a moisture permeable sheet 320 and a microneedle sheet 310.

A transdermal patch 1E illustrated in FIG. 18 is manufactured principally through a microneedle sheet affixing process, wherein the microneedle sheet 310 is affixed to the first area Ar1 of the moisture permeable sheet 320, and an assembling process, wherein a reinforcing film 30E is attached on. First, the water soluble microneedle sheet 310, wherein a plurality of water soluble microneedles 311 that have already been dried are formed in an array, is prepared. Furthermore, the microneedle sheet 310 is adhered by attaching a substrate 312 onto the adhesive layer 322 in the first area Ar1 of the moisture permeable sheet 320, wherein the adhesive layer 322 for adhering to the skin is formed over the entire surface of a skin opposing surface 320a opposing the skin. As in the moisture permeable sheets 20, 21A described above, the moisture permeable sheet 320 likewise comprises the polyurethane film 321, which has at least one of numerous vapor permeating holes, which pass water vapor therethrough and have a hole diameter of 0.1 μm to 100 μm and preferably of 10 μm to 30 μm, and numerous openings, which have an opening diameter of 0.5 mm or greater and less than 4.5 mm. In addition, in the moisture permeable sheet 320, the adhesive layer 322 for attaching onto the skin has the skin opposing surface 320a. The moisture permeable sheet 320 is configured to pass water vapor through the adhesive layer 322 and the vapor permeating holes of the polyurethane film 321 and such that the skin does not become sweaty at the location at which the moisture permeable sheet 320 is attached on. On that account, for example, the adhesive layer 322 is sparsely applied such that the application surface area is small so that the adhesive layer 322 does not block all the vapor permeating holes.

Next, the reinforcing film 30E, which includes the water vapor barrier sheet 31 that blocks the passage of water vapor through the first area Ar1, is attached on via the adhesive layer 35. At this time, the water vapor barrier sheet 31 is disposed such that it covers the third area Ar3, which includes the first area Ar1 and its surrounding area. As described above, the reinforcing film 30E integrally includes the water vapor barrier sheet 31 and the removable portion 32, which is disposed around the water vapor barrier sheet 31. Accordingly, it is possible to simultaneously impart a reinforcing function and a water vapor barrier function in one procedure wherein the one reinforcing film 30E is attached onto the moisture permeable sheet 320.

Figure 19:
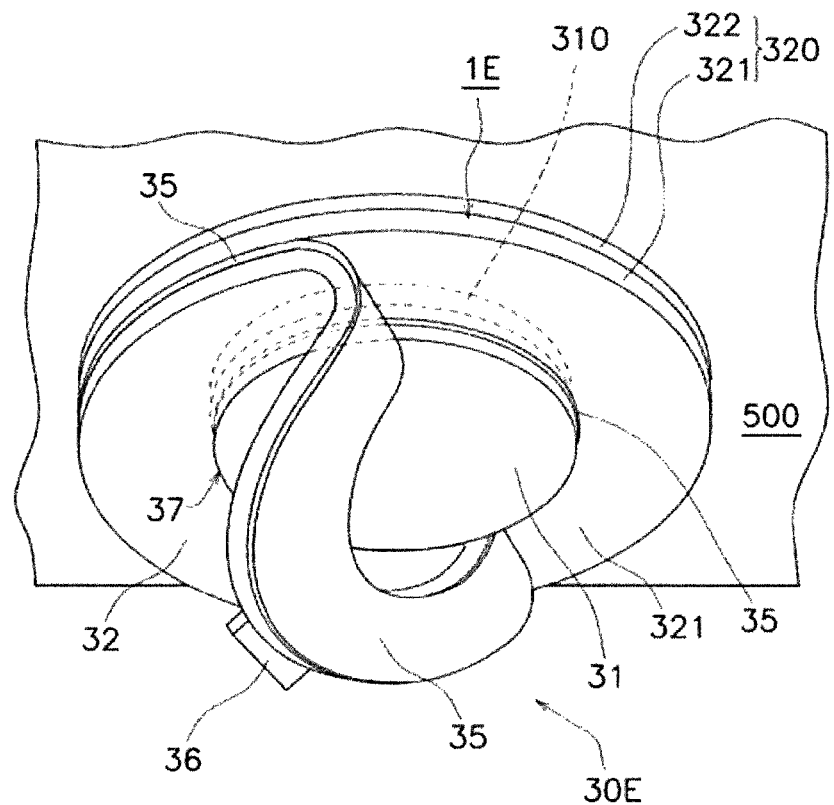
FIG. 19 is an oblique view for explaining a state wherein a removable portion of the transdermal patch illustrated in FIG. 18 is being peeled off.

The reinforcing film 30E illustrated in FIG. 18 differs from the reinforcing film 30 according to the first embodiment in that the reinforcing film 30E has a tab 36. The tab 36 is attached to the removable portion 32 and is a portion that is grabbed in order to make it easy to peel the removable portion 32. As illustrated in FIG. 19, if the tab 36 is held and pulled in a state wherein the cover film 40 has been removed from the transdermal patch 1E and the adhesive layer 322 is attached onto a skin 500, then, because the adhesive strength of the adhesive layer 35 is weaker, the removable portion 32 alone can be peeled off with the moisture permeable sheet 320 attached onto the skin 500 as is. At this time, the water vapor barrier sheet 31 and the removable portion 32 are separated with a separating line 37 as the boundary, and thereby the removable portion 32 alone can be peeled off. Consequently, the transdermal patch 1E can be attached onto the skin in the state wherein the microneedles 311 are securely pressed against the skin.

Furthermore, the reinforcing film 30 described above, wherein the tab 36 is not provided, can also be used as the reinforcing film.

In addition, the substrate 312 of the microneedle sheet 310 may include a porous layer like the porous sheet base material 29 explained in the fifth embodiment, or the entire substrate 312 may be porous.

(7) Features 7-1

In the transdermal patch manufacturing method according to the first embodiment, in the adhesive layer forming process explained with reference to FIG. 4 or in an alternative adhesive layer forming process used instead, prior to the completion of the assembling process explained with reference to FIG. 9 and FIG. 10, the adhesive agent is formed on the moisture permeable sheet 20 in the second area Ar2 outside of the first area Ar1 (one example of a raw materials aqueous solution contact area) that contacts the raw materials aqueous solution 110. In the adhesive layer forming process, the adhesive layer 22 (one example of a first adhesive layer) should be formed prior to the completion of the assembling process; therefore, for example, the adhesive layer may be formed on the cover film 40, or the adhesive layer may be formed simultaneously with the attaching of the cover film 40 onto the moisture permeable sheet 20. In addition, prior to the assembling process, a process may be provided wherein the adhesive agent is applied to the polyurethane film 21 of the moisture permeable sheet 20 and that process can also serve as the adhesive layer forming process. In the second through fifth embodiments, the process of preparing the moisture permeable sheet 20A, 20B, 20C, 20D, which includes the adhesive layer 22, 22C, on the polyurethane film 21, 21A serves as the adhesive layer forming process, similar to that of the first embodiment.

In the applying process explained with reference to FIGS. 5A and 5B, the raw materials aqueous solution 110 of the microneedles 11 is applied to the stamper 100, which has the micro through holes 101 for forming the microneedles 11. The first embodiment explained the applying process wherein application is performed just once, but the microneedle sheet 10 can also be formed as a multilayer structure by repetitively performing the applying process and the drying process multiple times.

In the mounting process explained with reference to FIG. 6, the moisture permeable sheet 20 is brought into contact with and mounted on the raw materials aqueous solution 110 such that the applied raw materials aqueous solution 110 mates with and is sandwiched by the stamper 100 and the moisture permeable sheet 20. The moisture permeable sheet 20 has the vapor permeating holes and therefore can pass therethrough the water vapor of the raw materials aqueous solution 110. In FIG. 6, the moisture permeable sheet 20 is below the stamper 100, but the moisture permeable sheet 20 may also be mounted on the stamper 100.

In the drying process explained with reference to FIGS. 7A and 7B, the raw materials aqueous solution 110 is dried in the state wherein the raw materials aqueous solution 110 is sandwiched between the stamper 100 and the moisture permeable sheet 20. In the drying process, substantially all of the moisture of at least the raw materials aqueous solution 110 passes through the moisture permeable sheet 20 and is evaporated, and the dried body of the raw materials aqueous solution 110 forms the microneedle sheet 10 having the microneedles 11. However, some of the moisture of the raw materials aqueous solution 110 may be transpired from, for example, the skin opposing surface 20a side of the moisture permeable sheet 20. In addition, in the drying process, as illustrated in FIG. 12, the openings 26 may be provided in the moisture permeable sheet 20 and the water vapor may be transpired through the openings 26.

In the peeling process explained with reference to FIG. 8, the stamper 100 is peeled off the microneedles 11 formed in the drying process. In the example illustrated in FIG. 8, the separation of the microneedles 11 and the stamper 100 is performed by peeling the stamper 100 off the microneedle sheet 10.

In the assembling process explained with reference to FIG. 9 and FIG. 10, the transdermal patch 1 is assembled using the moisture permeable sheet 20. In other words, when the reinforcing film 30 and the cover film 40 are attached to the moisture permeable sheet 20, they become the transdermal patch 1. The drying process fixes the microneedles 11 and forms the adhesive layer 22, which is for adhering to the skin, on the moisture permeable sheet 20. In the transdermal patch manufacturing method according to the second through fifth embodiments, the transdermal patches 1A, 1B, 1C, 1D are obtained, using the moisture permeable sheets 20A, 20B, 20C, 20D instead of the moisture permeable sheet 20, through the applying process, the mounting process, the drying process, the peeling process, and the assembling process.

In the drying process, the microneedles 11 are formed by passing the water vapor through the moisture permeable sheet 20, 20A, 20B, 20C, 20D and consequently are dried in the state wherein the microneedle sheet 10 (one example of the dried body) of the raw materials aqueous solution 110 is brought into direct contact with the moisture permeable sheet 20, 20A, 20B, 20C, 20D. Thus, because of the bonding agent layer and the adhesive layer, the microneedle sheet 10 can be affixed to the moisture permeable sheet 20, 20A, 20B, 20C, 20D without the microneedle sheet 10 and the moisture permeable sheet 20, 20A, 20B, 20C, 20D, which sandwich the bonding agent layer and the adhesive layer, separating. Consequently, by omitting the bonding agent layer for adhering the microneedles 11 to the moisture permeable sheet 20, 20A, 20B, 20C, 20D, it is easy to manufacture the transdermal patch 1 such that it is easy to be formed thinly, and the transdermal patch 1 is easy to be attached onto the skin and is not conspicuous even when attached onto the skin. In addition, as explained with regard to the transdermal patch 1D, if moisture from outside of the moisture permeable sheet 20D contacts the microneedles 11, then it is easy to make the moisture reach the microneedles 11 because the distance from the moisture permeable sheet 20D to the microneedle sheet 10 is short, which makes it easy to manufacture the transdermal patch 1 such that it is easy to impart moisture. Furthermore, in the peeling process, if the microneedles are peeled off the stamper, then a state is obtained wherein the microneedles 11 are adhered to the moisture permeable sheet 20, 20A, 20B, 20C, 20D, and therefore the process of bonding the microneedles 11 to the moisture permeable sheet 20, 20A, 20B, 20C, 20D is omitted, which improves productivity.

7-2

The moisture permeable sheet 20, 20B, 20C, 320 according to the first, third, fourth, and sixth embodiments comprises the polyurethane film 21, 21A, 21C, 321 (one example of the plastic film having a plurality of vapor permeating holes with a hole diameter of 0.1 µm to 100 µm). The preferable hole diameter of the polyurethane film 21, 21A, 21C, 321 is 10 µm to 30 µm.

Although not explained in the first through fifth embodiments, the moisture permeable sheet 20 may comprise a plastic film having both the plurality of vapor permeating holes with a hole diameter of 0.1 µm to 100 µm and the plurality of openings with an opening diameter of 0.5 mm or greater and less than 4.5 mm. For example, a polyurethane film of the type wherein the openings 26 are formed over the entire surface of the polyurethane film 21A corresponds to such a film. The moisture permeable sheet may comprise a plastic film having only the plurality of openings with an opening diameter of 0.5 mm or greater and less than 4.5 mm. In addition, the moisture permeable sheet may include the fiber sheet.

Thus, by using the polyurethane film 21, 21A, 21C, 321 having the vapor permeating holes, the openings 26, and the like, or the fiber sheet in the moisture permeable sheet 20, 20A, 20B, 20C, 20D, 320, when the moisture permeable sheet 20, 20A, 20B, 20C, 20D, 320 is attached onto the skin, the water vapor from the skin can pass through. Consequently, it is possible to manufacture the transdermal patch 1, 1A, 1B, 1C, 1D, 1E such that it does not get moist, even without, for example, modifying the properties of the moisture permeable sheet 20, 20A, 20B, 20C, 20D, 320, and to provide at low cost the transdermal patch 1, 1A, 1B, 1C, 1D, 1E that does not get moist.

7-3

In the drying process, as illustrated in FIGS. 7A and 7B, FIG. 12, and the like, the moisture permeable sheet 20, 20A is vacuum chucked to the flat pedestal 202, and therefore the moisture permeable sheet 20, 20A can be dried while held flat. Thereby, it is possible to prevent the warping of the microneedle sheet 10 (one example of a dried body of the raw materials aqueous solution) when the moisture permeable sheet 20, 20A is being dried, and the transdermal patch 1, 1A, comprising the flat moisture permeable sheet 20, 20A, can be produced efficiently. As described above, the moisture permeable sheets 20B, 20C, 20D according to the third through fifth embodiments are handled in the same manner as in the first and second embodiments and exhibit the same effects.

Furthermore, the method of holding the moisture permeable sheet 20, 20A flat is not limited to the method in which the moisture permeable sheet 20, 20A is vacuum chucked to the flat pedestal 202; for example, a configuration may also be adopted in which the moisture permeable sheet is fixed, by a clamp or the like, onto a flat plate shaped member.

7-4

In the moisture permeable sheet 20D according to the fifth embodiment, the moisture permeable sheet 20D has the porous sheet base material 29. The sheet shaped base material 29 is coated with the raw materials aqueous solution in a sheet shape and is dried in advance in the process corresponding to the bonding agent forming process (refer to FIG. 4) according to the first embodiment. The sheet shaped base material 29 is formed in the first area Ar1 and, in the mounting process, contacts the raw materials aqueous solution 110 (refer to FIG. 6). The drying process includes the process of forming the microneedles 11, wherein the sheet shaped base material 29 is dried in the state where the sheet shaped base material 29 is brought into contact with the raw materials aqueous solution 110 filling the minute holes. Thereby, when drying, the moisture from the raw materials aqueous solution 110 can be made to be absorbed by the sheet shaped base material 29 in contact with the raw materials aqueous solution 110, which makes it possible to increase the production speed.

7-5

The moisture permeable sheet 20C according to the fourth embodiment comprises the water absorbing sheet 27 (one example of a water absorbing layer) on the polyurethane film 21C having the plurality of vapor permeating holes, the hole diameter of which is 0.1 µm to 100 µm and preferably is 10 µm to 30 µm, and the plurality of openings 26, the opening diameter of which is 0.5 mm or greater and less than 4.5 mm. The water absorbing sheet 27 contacts the raw materials aqueous solution 110 in the mounting process. The water absorbing sheet 27 comprises the fiber sheet, the water absorbing macromolecular sponge sheet, or the like. That is, the water absorbing sheet 27 comprises the water absorbing layer, which is made of the fiber sheet, or the water absorbing layer containing water absorbing macromolecule. The drying process includes the process of forming the microneedles 11, wherein the water absorbing sheet 27 is dried in the state where the water absorbing sheet 27 is brought into contact with the raw materials aqueous solution 110 (refer to FIG. 6) filling the micro through holes 101. If the transdermal patch manufacturing method is configured as in the fourth embodiment, then, when drying, the water absorbing sheet 27 in contact with the raw materials aqueous solution 110 can be made to absorb the moisture, which makes it possible to increase the production speed.

7-6

The transdermal patch 1, 1A, 1B, 1C, 1D, 1E according to the first through sixth embodiments comprises the microneedle sheet 10, 310, the moisture permeable sheet 20, 20A, 20B, 20C, 20D, 320, and the water vapor barrier sheet 31. The microneedle sheet 10, 310 comprises the water soluble, sheet shaped substrate 12, 312 and the plurality of the water soluble microneedles 11, 311, which are formed in an array on the sheet shaped substrate 12, 312. In the moisture permeable sheet 20, 20A, 20B, 20C, 20D, 320, the microneedle sheet 10, 310 is affixed to the first area Ar1 on the skin opposing surface 20a, 320a side opposing the skin. In addition, in the moisture permeable sheet 20, 20A, 20B, 20C, 20D, 320, the adhesive agent is applied to the second area Ar1 outside of the first area Ar1 on the skin opposing surface 20a, 320a side. Furthermore, the moisture permeable sheet 20, 20A, 20B, 20C, 20D, 320 comprises the polyurethane film 21, 21A, 21C (example of the fiber sheet or the plastic film having in a first area at least one of the vapor permeating holes of from 0.1 μm to 100 μm and the plurality of openings having an opening diameter of 0.5 mm or greater and less than 4.5 mm) and passes water vapor therethrough.

The water vapor barrier sheet 31, which constitutes the transdermal patch 1, 1A, 1B, 1C, 1D, 1E configured in this manner, is formed on the outer surface 20b, 320b of the moisture permeable sheet 20, 20A, 20B, 20C, 20D, 320 opposite the skin opposing surface 20a, 320a and blocks the water vapor that attempts to reach the outer part from the outer surface 20b, 320a side in the entire first area Ar1 and in the third area A3, which includes the area around the first area Ar1.

According to the transdermal patch 1, 1A, 1B, 1C, 1D, 1E configured in this manner, when the transdermal patch 1, 1A, 1B, 1C, 1D, 1E is attached onto the skin, the water vapor that is given off by the skin and that passes through the gap between the microneedle sheet 10, 310 and the vapor permeating holes of the moisture permeable sheet 20, 20A, 20B, 20C, 20D, 320, the fiber, or the like is blocked by the water vapor barrier sheet 31. Consequently, the water vapor given off by the skin becomes available to be used by the water vapor barrier sheet 31, and thereby moisture can be supplied to the microneedle sheet 10, 310, which can promote the dissolving of the microneedle sheet 10, 310. In addition, it is possible to prevent the moisture permeable sheet 20, 20A, 20B, 20C, 20D, 320 from deforming owing to the water vapor barrier sheet 31 and to prevent the microneedle sheet 10, 310, which is affixed to the moisture permeable sheet 20, 20A, 20B, 20C, 20D, 320, from being peeled off owing to the deformation of the moisture permeable sheet 20, 20A, 20B, 20C, 20D, 320.

7-7

The transdermal patch 1, 1A, 1B, 1C, 1D, 1E according to the first through sixth embodiments comprises the reinforcing film 30, 30E, which is adhered onto the outer surface 20b, 320b of the moisture permeable sheet 20, 20A, 20B, 20C, 20D, 320, covers the portions at which the moisture permeable sheet 20, 20A, 20B, 20C, 20D, 320 overlaps the second area Ar2, and is formed of a plastic film, such as polypropylene, polyethylene, polyester, or the like, having a loop stiffness value larger than that of the moisture permeable sheet 20, 20A, 20B, 20C, 20D, 320. In the reinforcing film 30, 30E, the water vapor barrier sheet 31 is included as part of the corresponding reinforcing film 30, 30E, and the portion outside of the water vapor barrier sheet 31 is configured such that it can be peeled off during use. Furthermore, the reinforcing film 30, 30E is attached onto the moisture permeable sheet 20, 20A, 20B, 20C, 20D, 320 via the adhesive layer 35 (one example of a second adhesive layer) having an adhesive strength less than that of the adhesive layer 22, 322 (example of the first adhesive layer). Consequently, after the transdermal patch 1, 1A, 1B, 1C, 1D, 1E has been attached onto the skin, the removable portion 32 can be separated from the water vapor barrier sheet 31 and simply peeled off because the adhesive strength of the adhesive layer 22, 322 is greater than that of the adhesive layer 35. Consequently, the transdermal patch 1, 1A, 1B, 1C, 1D, 1E can be attached onto the skin in the state where the microneedles 11, 311 are pressed firmly against the skin.

In the transdermal patch 1, 1A, 1B, 1C, 1D, 1E, the reinforcing film 30, 30E is maintained in a shape that makes it easy to hold the transdermal patch 1, 1A, 1B, 1C, 1D, 1E, which makes it possible to solve problems such as the moisture permeable sheet 20, 20A, 20B, 20C, 20D, 320 deforming and thus making it difficult to attach the transdermal patch 1, 1A, 1B, 1C, 1D, 1E onto the skin. In addition, the water vapor barrier sheet 31 can also be used in combination as part of the reinforcing film 30, 30E, and therefore the water vapor barrier sheet 31 and the reinforcing film 30, 30E do not overlap, which makes it possible to prevent the thickness of the transdermal patch 1, 1A, 1B, 1C, 1D, 1E from increasing. In addition, by integrally adhering the water vapor barrier sheet 31 and the reinforcing film 30, 30E to the moisture permeable sheet 20, 20A, 20B, 20C, 20D, 320, it becomes easy to manufacture the transdermal patch 1, 1A, 1B, 1C, 1D, 1E.

7-8

The cover film 40 of the transdermal patch 1, 1A, 1B, 1C, 1D, 1E is adhered to the moisture permeable sheet 20, 20A, 20B, 20C, 20D, 320 by the adhesive agent and, together with the reinforcing film 30, 30E, forms the cavity CA, which envelops the microneedle sheet 10, 310 such that the cover film 40 does not contact the microneedle sheet 10, 310. Adopting such a configuration makes it possible to prevent damage to the microneedle 11, 311 by the cover film 40 and the reinforcing film 30, 30E during transport and the like of the transdermal patch 1, 1A, 1B, 1C, 1D, 1E and to prevent a reduction in the functions of the transdermal patch 1, 1A, 1B, 1C, 1D, 1E owing to damage to the microneedles 11, 311.

(8) Modified Example 8-1

Figure 20:
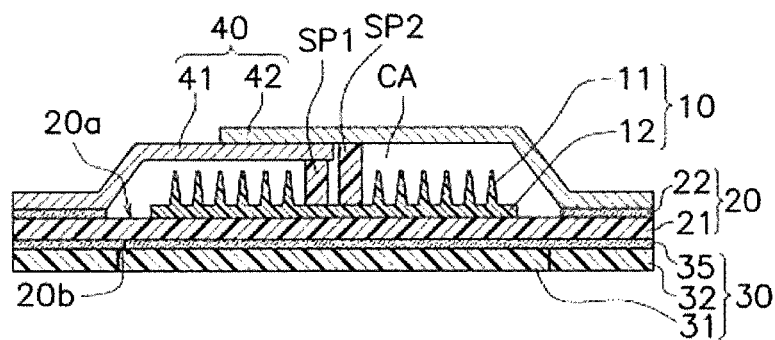
FIG. 20 is a schematic cross sectional view that illustrates one example of a cross sectional structure of the transdermal patch according to a modified example.

In the abovementioned first through sixth embodiments, there is no spacer between the moisture permeable sheet 20, 20A, 20B, 20C, 20D, 320, the microneedle sheet 10, and the like, and the cover film 40 inside the cavity CA formed by the cover film 40; however, as illustrated in FIG. 20, spacers SP1, SP2 for maintaining the cavity CA may be adopted. The spacers SP1, SP2 are plastic ribs formed in both the lower side cover film 41 and the upper side cover film 42. The spacers SP1, SP2 illustrated in FIG. 20 contact the microneedle sheet 10, but the present invention is not limited to such an embodiment; for example, the cavity CA may be supported by the spacers being brought into contact with the moisture permeable sheet 20, 20A, 20B, 20C, 20D, 320.

8-2

Figure 21:
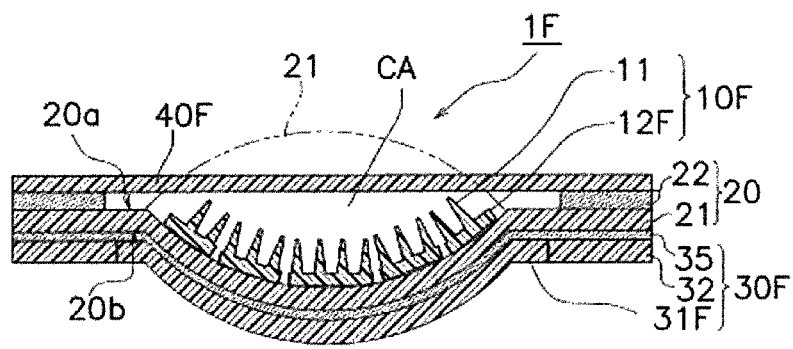
FIG. 21 is a schematic cross sectional view that illustrates another example of a cross sectional structure of the transdermal patch according to the modified example.

In the abovementioned first through sixth embodiments, the cavity CA is created by forming the cover film 40 in a dome shape; however, as in a transdermal patch 1F illustrated in FIG. 21, the cavity CA may be formed by making a cover film 40F flat and, moreover, providing a dome shaped portion on a water vapor barrier sheet 31F of a reinforcing film 30F.

The dome shaped portion of the water vapor barrier sheet 31F is made to protrude toward the skin opposing surface 20a side during manufacture, and the polyurethane film 21 is made into the shape indicated by the chain double dashed line. Moreover, during transport, the dome shaped portion of the water vapor barrier sheet 31F protrudes toward the outer surface 20b side, as illustrated in FIG. 21. Furthermore, during use, the dome shaped portion of the water vapor barrier sheet 31F is pressed by, for example, a finger, and thereby is made to protrude toward the skin opposing surface 20a side indicated by the chain double dashed line. Thereby, it becomes easy to press the microneedles 11 against the skin. Furthermore, a substrate 12F of a microneedle sheet 10F illustrated in FIG. 21 is split up so that it can easily track the deformation of the water vapor barrier sheet 31F of this type.

8-3

Figure 22:
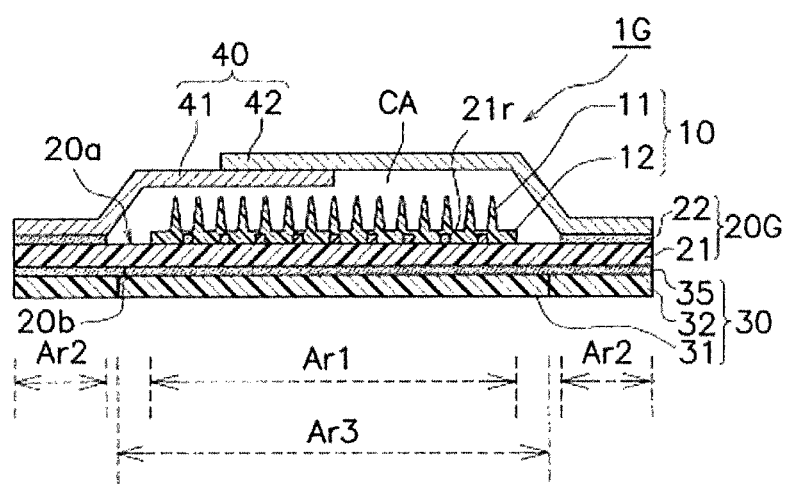
FIG. 22 is a schematic cross sectional view that illustrates another example of a cross sectional structure of the transdermal patch according to the modified example.

In the abovementioned first through sixth embodiments, nothing is formed in the first area Ar1 of the polyurethane film 21, 21A, 21C, 321 of the moisture permeable sheet 20, 20A, 20C, 20D, 320, and the first area Ar1 is in a flat state; however, for example, projections like ribs 21r of a transdermal patch 1G illustrated in FIG. 22 may be formed. When such ribs 21r are present, the affixing strength of the microneedle sheet 10 to the moisture permeable sheet 20, 20A, 20C, 20D or the adhesive layer 322 improves owing to the anchoring effect. In addition, if the microneedle sheet 10 is split up into multiple parts by something like the ribs 21r, stress is relieved and therefore the microneedle sheet 10 tends not to warp after drying.

The above explained the transdermal patch manufacturing method, the transdermal patch, and the like according to the first through sixth embodiments of the present invention and the modified examples thereof, but the present invention is not limited to the abovementioned embodiment and it is understood that various modifications may be effected within a scope that does not depart from the spirit of the invention. In particular, the embodiments and modified examples described in the present specification can be arbitrarily combined as needed.

8-4

The moisture permeable sheet 320 of the sixth embodiment may have a water absorbing sheet (one example of the water absorbing layer), such as the water absorbing sheet 27 of the fourth embodiment, on the polyurethane film 321 having a plurality of vapor permeating holes with a hole diameter of 0.1 μm to 100 μm and preferably 10 μm to 30 μm and a plurality of openings 26 having an opening diameter of 0.5 mm or greater and less than 4.5 mm. When such a water absorbing sheet is provided, the microneedle sheet 310 is affixed to the moisture permeable sheet 320 in the microneedle sheet affixing process such that the water absorbing sheet is disposed in the first area Ar1 and the microneedle sheet 310 contacts the water absorbing sheet. For example, one wherein the water absorbing sheet is formed on a rear surface of the microneedle sheet 310 is attached onto the adhesive layer 322. The water absorbing sheet comprises, for example, a fiber sheet, a water absorbing macromolecular sponge sheet, or the like. If manufactured in this manner, then the microneedle sheet 310, which contacts the water absorbing sheet in the first area Ar1, can be simply implemented, and the water absorbing sheet that plays the role of, for example, water holding by the microneedle sheet 310, can be provided simply.

The invention claimed is:

1. A transdermal patch comprising:
   a microneedle sheet having a water soluble sheet shaped substrate and a plurality of water soluble microneedles formed in an array on the substrate;
   a moisture permeable sheet passing therethrough water vapor and being made of a fiber sheet or a plastic film, the plastic film having at least one of vapor permeating holes and a plurality of openings, and the microneedle sheet being affixed to a first area on a skin opposing surface side opposing a skin and having a first adhesive layer applied to the skin opposing surface side; and
   a reinforcing film adhered, by a second adhesive layer, to an outer surface of the moisture permeable sheet, the outer surface being on the side opposite the skin opposing surface, and
   the reinforcing film including a water vapor barrier sheet and a removable portion that are separated by a separating line, the water vapor barrier sheet covering a first area of the outer surface and the removable portion covering a second area of the outer surface, and the removable portion being configured to detach from the second area of the outer surface to expose the second area of the outer surface while the water vapor barrier sheet remains on the first area of the outer surface to continue blocking passage of water vapor through the first area of the outer surface and the first area of the skin opposing side surface.

2. The transdermal patch according to claim 1, wherein the moisture permeable sheet comprises the plastic film, the plastic film having at least one of a plurality of the vapor permeating holes each with a hole diameter of 0.1 μm to 100 μm, and the plurality of openings each with an opening diameter of equal to or greater than 0.5 mm and equal to or less than 4.5 mm.

3. The transdermal patch according to claim 1, wherein the moisture permeable sheet comprises a water absorbing layer made of the fiber sheet or a water absorbing layer containing water absorbing macromolecule, on the plastic film having at least one of a plurality of the vapor permeating holes each with a hole diameter of 0.1 μm to 100 μm, and the plurality of openings each with an opening diameter of equal to or greater than 0.5 mm and equal to or less than 4.5 mm.

4. The transdermal patch according to claim 1, wherein the moisture permeable sheet has a porous sheet base material that is formed by the drying of an application raw materials aqueous solution in a sheet shape to the moisture permeable sheet in advance and the porous sheet base material contacts the raw materials aqueous solution of the microneedles in a mounting process.

5. The transdermal patch according to claim 4, wherein the moisture permeable sheet comprises a water absorbing layer made of the fiber sheet or a water absorbing layer containing water absorbing macromolecule, on the plastic film having at least one of a plurality of the vapor permeating holes each with a hole diameter of 0.1 μm to 100 μm, and the plurality of openings each with an opening diameter of equal to or greater than 0.5 mm and equal to or less than 4.5 mm, and the water absorbing layer contacts the raw materials aqueous solution in the mounting process.

6. The transdermal patch according to claim 1, wherein the reinforcing film is formed of a material having a loop stiffness value larger than that of the moisture permeable sheet.

7. The transdermal patch according to claim 6, further comprising:
a cover film that is adhered to the moisture permeable sheet by an adhesive agent and, together with the reinforcing film, forms a cavity that envelops the microneedle sheet such that the cover film does not contact the microneedle sheet.

8. The transdermal patch according to claim 1, further comprising:
a cover film that is adhered to the moisture permeable sheet by an adhesive agent and, together with the reinforcing film, forms a cavity that envelops the microneedle sheet such that the cover film does not contact the microneedle sheet.

9. The transdermal patch according to claim 1, wherein the removable portion includes a water vapor barrier sheet that blocks the passage of water vapor through the second area of the outer surface while the removable portion is attached to the second area of the outer surface.

10. The transdermal patch according to claim 1, wherein the separating line surrounds an outer perimeter of the first area of the outer surface looking in a direction toward the first area of the outer surface.

11. The transdermal patch according to claim 1, wherein the first area of the outer surface is circular, and the separating line surrounds an outer circumference of the first area of the outer surface looking in a direction toward the first area of the outer surface.

* * * * *